(12) United States Patent
Margalit et al.

(10) Patent No.: US 8,394,250 B2
(45) Date of Patent: Mar. 12, 2013

(54) ELECTRO-BLOTTING DEVICES, SYSTEMS, AND KITS AND METHODS FOR THEIR USE

(75) Inventors: Ilana Margalit, Ramat Gan (IL); Uri Yogev, Yavne (IL); Itay Sela, Israel (IL); Yuri Katz, Katzrin (IL); Adam Sartiel, Kochav-Yair (IL)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/371,325

(22) Filed: Feb. 10, 2012

(65) Prior Publication Data

US 2012/0138465 A1     Jun. 7, 2012

Related U.S. Application Data

(63) Continuation of application No. 13/172,751, filed on Jun. 29, 2011, which is a continuation of application No. 11/465,850, filed on Aug. 21, 2006, now Pat. No. 8,268,149, which is a continuation of application No. 11/357,416, filed on Feb. 21, 2006, now Pat. No. 8,173,002.

(60) Provisional application No. 60/655,420, filed on Feb. 24, 2005, provisional application No. 60/774,231, filed on Feb. 17, 2006.

(51) Int. Cl.
*G01N 27/447* (2006.01)

(52) U.S. Cl. .......................... 204/464; 205/614

(58) Field of Classification Search ............... 204/464, 204/435, 614, 613, 462
See application file for complete search history.

(56) References Cited

U.S. PATENT DOCUMENTS

| | | | |
|---|---|---|---|
| 4,139,440 | A | 2/1979 | Chrambach et al. |
| 4,452,901 | A | 6/1984 | Gordon et al. |
| 4,589,965 | A | 5/1986 | Kreisher |
| 4,622,124 | A | 11/1986 | Kreisher et al. |
| 4,840,714 | A | 6/1989 | Littlehales |
| 4,889,606 | A | 12/1989 | Dyson et al. |
| 5,013,420 | A | 5/1991 | Schuette |
| 5,173,159 | A | 12/1992 | Dutertre |
| 5,256,772 | A | 10/1993 | Ohtomo |
| 5,356,772 | A | 10/1994 | Chan |
| 5,445,723 | A | 8/1995 | Camacho |

(Continued)

FOREIGN PATENT DOCUMENTS

| | | |
|---|---|---|
| JP | 2002-257721 | 9/2002 |
| WO | WO-2005/094539 | 10/2005 |

(Continued)

OTHER PUBLICATIONS

Bio Rad's overview of Western Blotting Kit.*

(Continued)

*Primary Examiner* — Alex Noguerola
*Assistant Examiner* — Gurpreet Kaur

(57) ABSTRACT

The invention provides a dry electroblotting system for dry blotting gels, in which the system includes an electroblotting transfer stack that comprises an analysis gel and a blotting membrane, an anode, a body of anodic gel matrix juxtaposed with the anode between the anode and the transfer stack, a cathode, and a body of cathodic gel matrix juxtaposed with the cathode between the cathode and the transfer stack, in which the anodic gel matrix and the cathodic gel matrix each comprise an ion source for electrophoretic transfer. The dry electroblotting system does not use any liquid buffers that are added to the system just before electroblotting (such as when the transfer stack is being assembled). The anode, the cathode, or both can be separate from a power supply and provided as part of a disposable electrode assembly that also includes a body of gel matrix that includes ions for electrophoretic transfer.

18 Claims, 10 Drawing Sheets

U.S. PATENT DOCUMENTS

| | | | |
|---|---|---|---|
| 5,482,613 | A | 1/1996 | Boquet |
| 6,162,338 | A | 12/2000 | Updyke et al. |
| 6,379,516 | B1 | 4/2002 | Cabilly et al. |
| 6,592,734 | B2 | 7/2003 | Chen |
| 6,602,661 | B1 | 8/2003 | Knezevic et al. |
| 2002/0012920 | A1 | 1/2002 | Gardner et al. |
| 2002/0157953 | A1 | 10/2002 | Chen |
| 2005/0000811 | A1 | 1/2005 | Luka |
| 2005/0009036 | A1 | 1/2005 | Montesclaros et al. |
| 2005/0121325 | A1 | 6/2005 | Updyke et al. |
| 2006/0272946 | A1 | 12/2006 | Margalit et al. |
| 2006/0278531 | A1 | 12/2006 | Margalit et al. |
| 2009/0026079 | A1 | 1/2009 | Margalit et al. |
| 2009/0183989 | A1 | 7/2009 | Yang et al. |
| 2010/0044229 | A1 | 2/2010 | Margalit et al. |

FOREIGN PATENT DOCUMENTS

| | | |
|---|---|---|
| WO | WO-2007/126506 | 11/2007 |
| WO | WO-2010/006318 | 1/2010 |

OTHER PUBLICATIONS

Daban, Joan-Ramon, "Fluorescent labeling of proteins with Nile red and 2-methoxy-2,4-diphenyl-3(2H)-furanone: Physicochemical basis and application to the rapid staining of sodium dodecyl sulfate polyacrylamide gels and Western blots," *Electrophoresis*, vol. 22, 2001; pp. 874-880.

Genscript Corporation, "One-Step Western Blot Kit".

Genscript Corporation, "One-Step Western Kit," Technical Manual No. 0184; pp. 1-5.

Invitrogen Corporation, "G8808-02," Invitrogen Catalog 2005.

Kurien, Biji T., et al., "Protein Blotting: a review", *Journal of Immunological Methods*, vol. 274, No. 1-2, Mar. 1, 2003; pp. 1-15.

Pachulski, et al., "Production of Tablet-Like Solid Bodies Without Pressure by Sol-Gel Processes," *Letters in Drug Design & Discovery*, vol. 4, 2007; pp. 78-81.

U.S. Appl. No. 11/357,416; Notice of Allowance mailed Jan. 4, 2012.

PCT/US06/005933, PCT International Search Report.

PCT/US06/005933, PCT Written Opinion.

PCT/US09/050333, International Search Report mailed Feb. 26, 2010.

PCT/US09/050333, International Preliminary Report on Patentability mailed on Jan. 20, 2011.

Zeng, "Polyethylene Glycol Significantly Enhances the Transfer of Membrane Immunoblotting," *Analytical Biochemistry*, vol. 189, 1990; pp. 197-201.

\* cited by examiner

ELECTRO-BLOTTING DEVICES, SYSTEMS, AND KITS AND METHODS FOR THEIR USE

RELATED APPLICATION CROSS-REFERENCE TO RELATED APPLICATIONS

This patent application is a continuation and claims the right of priority under 35 U.S.C. Å120 to U.S. application Ser. No. 13/172,751, filed Jun. 29, 2011, which is a continuation of U.S. application Ser. No. 11/465,850, filed Aug. 21, 2006, which is a continuation of U.S. application Ser. No. 11/357,416, filed on 21 Feb. 2006, which claims the benefit of priority of U.S. Provisional Patent Application No. 60/655,420 filed on 24 Feb. 2005, entitled "Disposable Dry Electro-blotting Electrodes, Methods for their Use and Dry Blotting," and U.S. Provisional Patent Application No. 60/774,231 filed on 17 Feb. 2006, entitled "Dry 10 Electro-blotting Devices, Systems, and Kits, and Methods for their Use" naming Ilana Margalit, Uri Yogev, Sela Itay, Yuri Katz, Adam Sartiel, and Tim Updyke as inventors. The content and subject matter of these patent applications are hereby incorporated by reference in their entireties, including all text and drawings.

FIELD OF THE INVENTION

The present invention relates generally to the field of gel blotting and more specifically to dry electroblotting compositions and methods.

BACKGROUND

The separation of molecular species using gel electrophoresis methods is well known in the art. Various molecular species, including, inter alia, proteins, peptides, oligonucleotides, DNA and RNA may be electrophoretically separated on a body of separating gel, based, inter alia, on their charge/mass ratio, dimensional characteristics and other properties. Methods of isoelectric focusing may also be used for molecular species separation, as is well known in the art.

It is often necessary or desired to transfer the electrophoretically separated molecular species or resolved components from the separating gel into another matrix or onto a support in order to perform additional desired steps or chemical reactions, or immunological characterization or other manipulations on the separated molecular species. A useful method known in the art for transferring such resolved or separated species from the gel into another matrix or onto a support is electro-blotting.

A review article entitled "Protein Blotting: A review" by B. T. Kurien and R. H. Scofield published in J. of Immunological methods, Vol. 274, pp. 1-15 (2003), incorporated herein by reference in its entirety, describes, inter alia, various protein blotting methods including wet and semi-dry electro-blotting methods.

U.S. Pat. Nos. 5,482,613, 5,445,723, 5,356,772, 4,889,606, 4,840,714, 5,013,420, and US Published Application 2002157953 disclose, inter alia, various types of apparatuses and methods for performing wet and semi-dry electrophoretic transfer, all the above cited US patents and published Patent Application are incorporated herein by reference in their entirety.

In electro-blotting, after electrophoretic separation of molecular species, the electrophoresis gel containing the separated molecular species is put in contact with a relatively thin matrix of a porous material, such as, among others, a nitrocellulose-based blotting membrane, a PVDF-based blotting membrane, an activated paper blotting membrane, an activated nylon blotting membrane or the like, and an electrical current is passed through the sandwiched gel and blotting membrane in a direction generally perpendicular to the surface of the blotting membrane. Some or most of the electrically charged molecular species may thus be electrophoretically transferred from the gel to the blotting membrane.

Current may be passed through the gel and blotting membrane combination by putting the gel and the blotting membrane between two suitable electrodes and applying a suitable voltage difference between the electrodes. One such electrode operates as a cathode and the other opposite electrode operates as the anode.

Typically, the electrical connection between the electrodes and the gel and blotting membrane is achieved by placing an electrically conducting buffer solution between the electrode and the gel and/or between the electrode and the blotting membrane. These buffer solution(s) serve as a source of ions for the electro-blotting. This method is known in the art as wet blotting. A disadvantage of wet blotting methods is the need for relatively cumbersome apparatus and the need to prepare and handle buffers, thus making the method time consuming.

Alternatively, one or more pieces of dry filter paper or another suitable type of dry porous material are put in contact with the blotting membrane and with the gel, the filter paper or other dry porous material is wetted with a buffer solution that serves as the ion reservoir for the transferring. The electrodes (cathode and anode) are put in contact with the buffer wetted filter paper(s) or other porous material and electro-blotting is performed.

While the semi-dry electro-blotting methods known in the art solve some of the problems of wet electro-blotting methods, they still have the disadvantage of requiring preparation and handling of liquid buffer solutions for wetting the filter papers and requiring handling and alignment of the filter papers with the gel and the blotting membrane. These methods are, therefore, still inconvenient and time consuming. Additionally, in semi-dry electro-blotting methods, the limited amount of ions in the buffer wetted filter paper may limit the amount of current that may be used, resulting in a relatively long electro-blotting time. Commercially available semi-dry blotters are typically limited to current densities in the range of 2-6 milliamperes per square centimeter (2-6 $mA/cm^2$).

SUMMARY OF THE INVENTION

The present invention is based, in part, on the discovery that a reservoir of ions for electrophoretic transfer can be provided in gel matrices positioned between an anode of an electroblotting system and one side of a separating gel/blotting membrane transfer stack, and between a cathode of the electroblotting system and the other side of the transfer stack, allowing electroblotting to be performed with no liquid buffers other than those provided within the gel matrices positioned adjacent to and in contact with the electrodes of the system. Using this dry-blotting system, proteins, nucleic acids, and other biomolecules are transferred from a separating gel to a blotting membrane much more efficiently and rapidly than traditional electroblotting, and no liquid buffer handling is required by a user performing the electroblotting method. For example, using an electroblotting system provided herein, an electroblotting transfer can be performed in as little as 5 or 10 minutes. Furthermore, in certain aspects of the invention, an electrode of the electroblotting system is provided that creates fewer bubbles during electroblotting.

Anodic and/or cathodic gel matrix ion reservoirs can be provided to a customer in pre-made, disposable form for use in a dry-blotting system. The pre-made, disposable anodic and/or cathodic gel matrix ion reservoir can be enclosed within in a sealed package. Furthermore, multiple anodic and/or cathodic gel matrix ion reservoirs can be enclosed together in packaging.

Provided herein in another aspect is electrode assemblies for performing dry electroblotting, in which the electrode assemblies include a body of gel matrix that includes a source of ions; and an electrically conducting electrode associated with the body of gel matrix. In certain embodiments, the electrode is attached to the body of gel matrix. In certain embodiments, the electrically conducting electrode is at least partially embedded in the body of gel matrix. In certain embodiments, the body of gel matrix is juxtaposed with the conducting electrode in a plastic tray before and during electrophoretic transfer. The electrode assembly can be enclosed in a sealed package. An electrode used in the dry electroblotting systems and electrode assemblies provided herein can be, for example, a layer that includes a non-metallic electrically conducting material, a mesh comprising a non-metallic electrically conducting material, a metal foil, a metal mesh, non-conducting polymer coated with a conducting metal or non-metal, and/or combinations thereof. An electrode of a nonconducting material coated with a conducting material can be in the form of a sheet, mesh, or other structure. In certain embodiments, an electrode of an electrode assembly comprises an electrochemically ionizable metal such as lead, copper, silver or combinations thereof. In certain embodiments, an electrode of an electrode assembly comprises aluminum or palladium.

An electrode assembly that includes an electrode in association with a gel matrix ion reservoir for dry electroblotting can also be provided to a customer in a pre-made, disposable form, thereby making it easy for a customer to use the electrode assembly, and providing an effective business model. The electrode is juxtaposed with a body of gel matrix, and can be provided in a tray or holder. The electrode assembly can be enclosed in a sealed package. The present invention also provides embodiments wherein the electrode assembly provides additional functionality. For example, staining compounds, molecules for blocking non-specific binding, reducing agents, or proteases can be included in the electrode assembly, to facilitate analysis of molecular species separated within a separating gel.

In a further aspect, the invention provides a dry electroblotting system, in which the system includes an electroblotting transfer stack that comprises an analysis gel and a blotting membrane, an anode, a body of anodic gel in contact with the anode and positioned between the anode and the transfer stack, a cathode, and a body of cathodic gel matrix in contact with the cathode and positioned between the cathode and the transfer stack, in which the anodic gel matrix and the cathodic gel matrix each comprise an ion source for electrophoretic transfer. The dry electroblotting system does not require any liquid buffers to be added to the system just before electroblotting (such as when the transfer stack is being assembled). In some preferred embodiments, the system is assembled such that the anodic gel matrix and anode are on the membrane side of the transfer stack, and the cathodic gel matrix and cathode are on the analysis gel side of the transfer stack. In some embodiments, the anode, the cathode, or both can be integral to a power supply. In some embodiments, the anode, the cathode, or both can be separate from a power supply.

The invention also includes an apparatus for dry blotting gels, in which the apparatus includes: a power supply that can hold a transfer stack, an anode, a body of anodic gel matrix juxtaposed with the anode between the anode and the transfer stack, a cathode, and a body of cathodic gel matrix juxtaposed with the cathode between the cathode and the transfer stack, during electrophoretic transfer. During electroblotting, the dry electroblotting apparatus does not include, hold, or connect to reservoirs for holding liquid buffers for electrophoretic transfer. In some embodiments, the anode and anodic gel matrix of the apparatus are provided as an anode assembly that can be reversibly positioned on or against or connected with electrical contacts of the apparatus. In some embodiments, one or both of the anode or cathode is integral to the apparatus.

The power supply of the apparatus includes an on/off switch, a power cord for connecting to a power source, and preferably an AC/DC adaptor. In some embodiments, the power supply of the dry electroblotting apparatus comprises display panel that indicate at least one of the voltage, current, elapsed time, or time remaining for an electrophoretic transfer. The power supply optionally includes software that includes a menu of electroblotting conditions. In some embodiments, the dry electroblotting apparatus comprises at least one universal serial bus (USB) port.

In another aspect, the invention provides a method of dry electroblotting, which includes passing an electric current between an anode and cathode of a dry electroblotting system that includes, in the following order: an anode, a body of anodic gel matrix, a blotting membrane, an analysis gel that comprises one or more biomolecules, a body of cathodic gel matrix, and a cathode to transfer one or more biomolecules from the analysis gel to the blotting membrane.

In certain illustrative aspects of the method, the anodic electrode is made of copper. In certain illustrative aspects, both the anodic and cathodic electrodes are made of copper. In some aspects, current density used to pass a current can be equal to or larger than 15 milliamperes per square centimeter of the first face of said separating gel.

The method can further include, prior to passing a current between the anodic and cathodic electrodes, passing the analysis gel, an anodic electrode assembly that includes the anode, a body of anodic gel matrix, and a blotting membrane, and a cathodic electrode assembly that includes a cathode and a body of cathodic gel matrix, through a de-bubbling device having gel separator members configured for reducing or avoiding the trapping of air bubbles between the separating gel, the blotting membrane, and the cathodic body of gel matrix.

In yet another aspect, provided herein are kits for performing dry electroblotting. In one embodiment, a kit includes at least one body of gel matrix that comprises an ion source for electrophoresis and at least one blotting membrane. In another embodiment, a kit includes at least one body of anodic gel matrix and at least one body of cathodic gel matrix. In another embodiment, a kit includes at least one body of gel matrix that includes at least one dye, detergent, modifying enzyme or reagent, or reducing compound. A body of anodic gel matrix and a body of cathodic gel matrix may be provided in a kit in sealed packages. Electroblotting gel matrix kits can also optionally further include at least one blotting membrane, at least one sheet of filter paper, at least one sponge, and/or at least one electrode.

In another aspect, a kit provides one or more disposable anodic electrode assemblies and/or one or more disposable cathodic electrode assemblies. In some embodiments, one or more anodic electrode assemblies can include a body of gel including a source of ions and an electrode juxtaposed with a body of gel matrix. In some embodiments, one or more cathodic electrode assemblies can include a body of gel including a source of ions and an electrode juxtaposed with a gel matrix. An anodic electrode assembly, a cathodic assembly, or both, can be provided in a tray, such as a plastic tray. A cathodic assembly can be provided in a tray, such as a plastic tray. An anodic electrode assembly provided in a kit can include one or more blotting membranes juxtaposed with a second side of the body of gel matrix.

The anodic and/or cathodic electrode assemblies can be enclosed within a sealed package together, or separately. Furthermore, multiple anodic and/or cathodic electrode assemblies can be enclosed together in packaging.

In some aspects, an electroblotting kit includes one or more disposable anodic electrode assemblies and one or more disposable cathodic electrode assemblies. In some aspects, an electroblotting kit includes one or more disposable anodic electrode assemblies and at least one body of cathodic gel matrix. The kits can optionally include one or more blotting membranes, sheets of filter paper, or sponges.

BRIEF DESCRIPTION OF THE DRAWINGS

The invention is herein described, by way of example only, with reference to the accompanying drawings, in which like components are designated by like reference numerals, wherein.

DETAILED DESCRIPTION OF THE INVENTION

Figure 1:
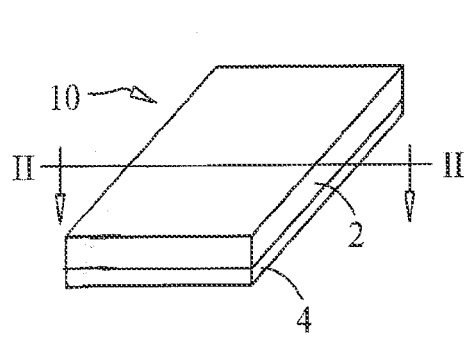
FIG. 1 is a schematic isometric view of a disposable dry electro-blotting electrode assembly, in accordance with an embodiment of the present invention.

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Terms of orientation such as "up" and "down", "top" and "bottom", or "upper" or "lower" and the like refer to orientation of parts during use of a device. Where a term is provided in the singular, the inventors also contemplate the plural of that term. Where there are discrepancies in terms and definitions used in references that are incorporated by reference, the terms used in this application shall have the definitions given herein. As employed throughout the disclosure, the following terms, unless otherwise indicated, shall be understood to have the following meanings:

The following terms are used throughout the application:

A "dry electroblotting electrode assembly" is an assembly that includes an electrode and a non-liquid ion source in contact with the electrode, in which the dry electroblotting electrode assembly allows electroblotting to be performed without requiring that liquid buffers are added to an electroblotting system before use. Rather, the electrode assemblies of a dry electroblotting system provide the ion source for electrophoretic transfer. A "non-liquid" ion source can be a solid or gel. The ion source of a dry electroblotting electrode assembly is preferably provided in a body of gel matrix. A dry electroblotting electrode assembly can also optionally include other components of a dry electroblotting system, for example, a blotting membrane.

"Dry electroblotting" is electroblotting performed using a solid or semi-solid ion source for electrophoresis. In some embodiments, dry electroblotting is performed without the addition of liquid buffers or solutions providing an ion source to the electroblotting system when assembling the transfer stack (a membrane positioned against an electrophoresis gel, and any filters, sponges, meshes, etc., surrounding or against the outside surfaces of the juxtaposed gel and membrane) prior to electroblotting. In some embodiments, one or more components of an electroblotting system, such as a piece of filter paper or blotting membrane, can be wetted prior to electroblotting, but the wetting is not required for providing ions that enable electrophoretic transfer A "disposable" electrode is an electrode that is intended to be used less than 10 times. A "disposable" electrode assembly is an electrode assembly that is intended to be used less than 10 times. In embodiments in which an electrode assembly includes a blotting membrane, a blotting membrane of an electrode assembly is typically used only once. In certain illustrative aspects, the entire disposable electrode assembly is intended to be used only once.

As used herein "electrochemically ionizable metal" is a metal that, when used as an electrode under standard electrophoresis conditions, ionizes in response to applied current. "Standard electrophoresis conditions" are conditions of between about 0 degrees Celsius and about 100 degrees Celsius, more preferably between about 0 degrees Celsius and about 80 degrees Celsius, and more preferably yet between about 2 degrees Celsius and about 50 degrees Celsius, in which the electrode is in contact with a conducting medium, such as a solution or gel. During electrophoresis (or electrophoretic transfer) ionization of an electrochemically ionizable metal electrode occurs in place of electrolysis of water at the electrode. Non-limiting examples of electrochemically ionizable metals include copper, silver, and lead.

An "analysis gel" is a gel that includes one or more biomolecules to be detected. The biomolecules can be, as non-limiting examples, polysaccharides, nucleic acids, or proteins, and can be purified, partially purified, or part of a mixture or sample. An analysis gel can be a gel to which biomolecules or samples or mixtures that include biomolecules have been applied to or electrophoreses or absorbed into without further separation, or an analysis gel can be a separating gel, such as an electrophoresis gel on which biomolecules have been separated on the basis of size, charge, or other properties.

An "electroblotting transfer stack" or simply, a "transfer stack" is a structure that includes an analysis gel and a blotting membrane, in which the blotting membrane is juxtaposed with the gel such that one of the two faces of the blotting membrane is in contact with one of the two faces of the gel. In exemplary embodiments, the analysis gel in a transfer stack is an electrophoresis gel, that is, a gel on which one or more biomolecules has been electrophoresed. The blotting membrane is typically nitrocellulose or another cellulose derivative, nylon, or polyvinylidene difluoride (PDVF) (or derivatized versions of any of these) to which a biomolecule can be transferred such that it reversibly or, preferably, irreversibly binds the membrane. A transfer stack can optionally also include other elements, such as, for example, filter paper placed against the non-gel face of the membrane or the non-membrane face of the gel.

As used herein, "juxtaposed with" means that two structures so referenced are positioned so as to be in side-by-side contact with one another. In the context of the present invention, juxtaposed structures are preferably in contact and aligned such that a major portion of a side or face of one structure is adjacent to and in continuous contact with a major portion of a side or face of the other structure. Juxtaposed structures may reversibly or irreversibly adhere to one another, for example by adhesives, chemical bonds, or mechanical fasteners. In some aspects, one juxtaposed structure may be attached to another by being at least partially embedded in the other structure. In some aspects, juxtaposed structures can be reversibly juxtaposed by being placed in the same holder where they are held by gravity, walls of the holder, or fasteners. In some aspects, juxtaposed structures can be reversibly juxtaposed by being held together by electrostatic forces such that the structures, such as a membrane and a body of gel, can be easily separated by a technician.

As used herein "anode compartment" refers an area of an electroblotting apparatus, device, or system that includes a source of ions for electroblotting that is in contact with the anode of the system, device, or apparatus. For example, an anode compartment can be a buffer tank that includes or is contacted by an anode and holds a solution comprising ions, filter paper soaked in a transfer buffer, or an anodic gel matrix.

As used herein "cathode compartment" refers an area of an electroblotting apparatus, device, or system that includes a source of ions for electroblotting that is in contact with the cathode of the system, device, or apparatus. For example, a cathode compartment can be a buffer tank that includes or is contacted by a cathode and holds a solution comprising ions, filter paper soaked in a transfer buffer, or a cathodic gel matrix.

A compound that is "preferentially provided", "preferentially present", or "preferentially used" in one compartment or component of an electroblotting system is a compound that is provided, present, or used in that compartment and either not provided, present, or used, in another compartment or component of the system, or present at significantly reduced amounts in another compartment or component of the system when compared with the amount of compound in the compartment or component the compound is preferentially provided, present, or used in. In some exemplary embodiments, a compound preferentially provided in an anode compartment of an electroblotting system is either not present or present in significantly reduced amounts in the cathode compartment of the system. In some exemplary embodiments, a compound preferentially provided in a cathode compartment of an electroblotting system is either not present or present in significantly reduced amounts in the anode compartment of the system.

As used herein, a compound present, used, or provided in "significantly reduced concentration" or "significantly reduced amount" means that the concentration of the anionic compound in the cathode compartment is 0.5× (50%) or less, preferably 0.2× (20%) or less, and more preferably 0.1× (10%) or less when compared with the concentration of the anionic compound in the anode compartment of an electroblotting system or apparatus.

Dry Electroblotting System

The invention provides a dry electroblotting system comprising an electroblotting transfer stack, an anode, a body of anodic gel matrix positioned between the anode and the electroblotting transfer stack, a cathode, and a body of cathodic gel matrix positioned between the cathode, in which the anodic gel matrix and the cathodic gel matrix each comprise an ion source for electrophoretic transfer. The transfer stack comprises at least one analysis gel that includes at least one biomolecule (such as, for example, a polysaccharide, a protein, a peptide, or a nucleic acid) and at least one blotting membrane juxtaposed with the analysis gel. In some embodiments, the dry electroblotting system does not use any liquid buffers that are added to the system before electroblotting (such as when the transfer stack is being assembled). In some embodiments, one or more components of the dry electoblotting system, such as a blotting membrane, or a sheet of filter paper placed between the analysis gel and a body of gel matrix or placed between the blotting membrane and a body of gel matrix, can be wetted prior to electroblotting. In a dry electroblotting system of the invention, however, wetting of a system component such as a blotting membrane or sheet of filter paper with water, a detergent solution, a buffer, or solution, is not necessary for providing ions required to drive electrophoretic transfer. In some embodiments, a gel can be equilibrated in a buffer or solution prior to electroblotting. Equilibrating a gel in a solution or buffer is not necessary for providing ions required to drive electrophoretic transfer in a dry electroblotting system.

The system is constructed such that when an electrical current is passed between the cathode and the anode, biomolecules are transferred from an analysis gel to a blotting membrane. The assembled system thus provides electrical continuity from the cathode to the anode, in which current passes from the cathode through the cathodic body of gel matrix, one or more analysis gels, one or more blotting membranes, and the anodic body of gel matrix to the anode. Thus, in a preferred embodiment, one side of the cathodic body of gel matrix is in contact with the cathode, and another side of the cathodic body of gel matrix is in direct or indirect electrical contact with an analysis gel of the transfer stack. One side of the anodic body of gel matrix is in contact with the anode, and another side of the anodic body of gel matrix is in direct or indirect electrical contact with a blotting membrane of the transfer stack.

In a variation of this configuration, a dry electroblotting system of the invention can have a blotting membrane juxtaposed with the cathode face of an analysis gel. In such a configuration, an additional blotting membrane can optionally also be juxtaposed with the anode face of the analysis gel. This configuration can be used, for example, when one or more biomolecules of interest in an analysis gel are expected to have positive charge under electrophoretic transfer conditions. In one example, the analysis gel can be a native gel on which proteins have been electrophoresed in the absence of a detergent or reagent that confers negative charge, in which case one or more of the proteins on the analysis gel may have a net positive charge and migrate toward the cathode during transfer. Negatively charged biomolecules in the same analysis gel can optionally be simultaneously blotted to a membrane provided on the anode side of the analysis gel.

An analysis gel can be of any irregular or regular shape, e.g., oval or circular, but is typically rectangular. An analysis gel can be of any feasible length and width, and has a thickness significantly less than the length or width dimensions of the analysis gel. For example, the thickness of an analysis gel can be 20% or less than the length or width, and is preferably 10% or less than the length or width, or preferably 5% or less than the length or width, or preferably 2% or less than the length or width of the analysis gel. An analysis gel used in a dry electroblotting system thus has two faces opposite one another defined by the length and width dimensions of the gel. An analysis gel can have any composition, and can be, as nonlimiting examples, an agar gel, a starch gel, an agarose gel, an acrylamide gel, a composite gel comprising one or more different polymers, etc. Illustrative nonlimiting examples of analysis gels that can be used in a dry electroblotting system are separating gels that can be poured by the user or pre-made, such as, but not limited to, Tris-glycine gels, NuPAGE® Bis Tris gels (Invitrogen, Carlsbad, Calif.), NuPAGE® Tris Acetate gels (Invitrogen, Carlsbad, Calif.), E-PAGE™ gels (Invitrogen, Carlsbad, Calif.), E-Gels® (Invitrogen, Carlsbad, Calif.), etc.

A first face of an analysis gel of a dry electroblotting system is juxtaposed with a first face of a blotting membrane, and the second face of the analysis gel is positioned in direct or indirect contact with an electrode assembly. In some embodiments, the second face of the analysis gel is in contact with a cathodic electrode assembly. If the contact between the gel and the cathodic electrode assembly is indirect (for example, wetted filter paper may be between the cathodic gel matrix and an analysis gel), the indirect contact provides electrical continuity between the analysis gel and the cathodic gel matrix. The stack is positioned such that the second face of the blotting membrane that is positioned against the first face of an analysis gel is in direct or indirect contact with the anodic gel matrix. If the contact between the blotting membrane and the anodic electrode assembly is indirect (for example, wetted filter paper may be between the anodic gel matrix and a blotting membrane), the indirect contact provides electrical continuity between the blotting membrane and the anodic gel matrix.

A wetted filter paper positioned between a gel stack and a body of gel matrix can be wetted in, for example, water, buffer, or a staining or detergent solution.

A transfer stack of a dry electroblotting system can comprise more than one analysis gel. For example, two or more analysis gels can be positioned side-by-side in a transfer stack. In cases where more than one analysis gel is provided in a transfer stack of a dry electroblotting system, more than one blotting membrane can optionally be used. For example, an individual blotting membrane can be juxtaposed with each analysis gel of the dry electroblotting system. In the alternative, a single blotting membrane can be juxtaposed with more than one analysis gel, such that biomolecules of two or more analysis gels are transferred to the same blotting membrane.

In preferred embodiments, an analysis gel and a blotting membrane of a dry electroblotting system have length and width dimensions that are the same or nearly the same (e.g., dimensions within 10%, 5%, or 2% of each other). A blotting membrane can be, for example, paper, a cellulose-based blotting membrane (such as but not limited to cellulose nitrate or cellulose acetate), a nitrocellulose-based membrane, a nylon-based membrane, or polyvinylidene difluoride (PVDF)-based membrane, or activated or derivatized versions of these (such as, for example, surface-charged derivatives). A blotting membrane in a dry electroblotting system is juxtaposed with an analysis gel such that a first face of the blotting membrane is in continuous surface contact with a first face of the analysis gel.

In some embodiments, the system further includes at least one piece of filter paper positioned between the analysis gel and the body of cathodic gel matrix.

A body of anodic gel matrix and a body of cathodic gel matrix of a dry electroblotting system can have the same or different compositions. For example, a body of anodic gel matrix and a body of cathodic gel matrix of a dry electroblotting system can have the same or different gel-forming polymers, or one or more common gel-forming polymers at different concentrations. A body of anodic gel matrix and a body of cathodic gel matrix of a dry electroblotting system can have the same or different buffers, or can have a common buffer present at different concentrations. An anodic gel matrix can comprises one or more additional compounds not present in the cathodic gel matrix. A cathodic gel matrix can comprises one or more additional compounds not present in the anodic gel matrix.

A body of gel matrix (a body of anodic gel matrix or a body of cathodic gel matrix) can comprise agarose, acrylamide, alumina, silica, starch or other polysaccharides such as chitosan, gums (e.g., xantham gum, gellan gum), carrageenan, pectin, or other polymers that form gels, or any combinations of these. In some preferred embodiments, the body of cathodic gel matrix comprises acrylamide, for example, at a concentration of from about 2.5% to about 30%, or from about 5% to about 20%. In some embodiments, the body of cathodic gel matrix comprises agarose, for example at a concentration of from about 0.1% to about 5%, or from about 0.5% to about 4%, or from about 1% to about 3%. In some preferred embodiments, the body of cathodic gel matrix comprises acrylamide and agarose, for example, a cathodic gel matrix can comprise from about 2.5% to about 30% acrylamide and from about 0.1% to about 5% agarose, preferably from about 5% to about 20% acrylamide and from about 0.2% to about 2.5% agarose.

A source of ions for electrophoretic transfer provided in an cathodic gel matrix or an anodic gel matrix can be from for example, a salt, acid, base, or buffer, or combinations thereof. Preferably, the body of cathodic gel matrix comprises at least one buffer, preferably an organic buffer. A buffer provided in the cathodic gel matrix can be a zwitterionic buffer. In preferred embodiments in which an analysis gel comprises proteins or peptide to be electroblotted, the body of cathodic gel matrix comprises a buffer having a pKa of between about 6.5 and about 8.5, and more preferably between about 7 and about 8. A buffer in the cathodic gel matrix can be present at a concentration of from about 10 mM to about 1 M, for example, at a concentration of between about 20 mM and about 500 mM, and in some embodiments between about 50 mM and about 300 mM.

For example, the body of cathodic gel matrix can comprise, as nonlimiting examples, 2-(N-morpholino)-ethanesulfonic acid (MES), N-(2-acetamido)-2-aminoethanesulfonic acid (ACES), piperazine-N,N'-2-ethanesulfonic acid (PIPES), 2-(N-morpholino)-2-hydroxy-propanesulfonic acid (MOPSO), N,N-bis-(hydroxyethyl)-2-aminoethanesulfonic acid (BES), 3-(N-morpholino)-propanesulfonic acid (MOPS), N-2-hydroxyethyl-piperazine-N-2-ethanesulfonic acid (HEPES), 3-(N-tris-(hydroxymethyl)methylamino)-2-hydroxypropanesulfonic acid (TAPSO), 3-(N,N-Bis[2-hydroxyethyl]amino)-2-hydroxypro panesulfonic acid (DIPSO), N-(2-Hydroxyethyl)piperazine-N'-(2-hydroxypropanesulfonic acid) (HEPPSO), 4-(2-Hydroxyethyl)-1-piperazine propanesulfonic acid (EPPS) N-[Tris(hydroxymethyl)-methyl]glycine (Tricine), N,N-Bis(2-hydroxyethyl)glycine (Bicine), (2-Hydroxy-1,1-bis(hydroxymethyl)ethyl)amino]-1-propanesulfonic acid (TAPS), N-(1,1-Dimethyl-2-hydroxyethyl)-3-amino-2-hydroxypropanesulfonic acid (AMPSO), tris(hydroxy methyl)amino-methane (Tris), or bis[2-hydroxyethyl]iminotris-[hydroxymethyl]methane (Bis-Tris).

The cathodic gel matrix, the anodic gel matrix, or both can optionally comprise an ion exchange matrix. For example, the anodic gel matrix can optionally comprise a cation exchange matrix. The cathodic gel matrix can optionally comprise an anion exchange matrix such as, but not limited to, DEAE cellulose. The ion exchange matrix can be loaded with ions, such as buffer ions, for example, a DEAE ion exchange matrix can be loaded with Tricine anions.

A cathodic gel matrix body can further include ethylene glycol, an alcohol, one or more detergents, one or more antifungal agents, one or more blocking agents, one or more anti-corrosion agents, one or more modifying agents or enzymes, proteases, reducing agents, etc. The body of cathodic gel matrix can comprise a dye, such as, for example, a nucleic acid or protein stain. For example, the body of cathodic gel matrix can comprise a dye such as, but not limited to, a SYPRO dye, a Coomassie dye, a Direct Blue dye, or a copper-based stain.

Many different types of protein and/or DNA stains or other stains for other types of separated molecular species may be included in the gel bodies of the electrode assemblies disclosed herein. Preferably, such stains may be anionic or cationic stains and may be suitably loaded into the anodic electrode assembly or the cathodic electrode assembly, respectively. It is also possible, in accordance with an additional embodiment of the present invention, to use in the same blotting assembly an anionic stain included in the cathodic electrode assembly and a cationic stain included in the anodic electrode assembly. When current is applied to the electrodes of such a blotting assembly, the anionic stain molecules migrate away from the cathode and towards the blotting membrane and simultaneously the cationic stain molecules also migrate away from the anode and towards the blotting membrane. The blotted molecular species at the blotting membrane may thus be stained by both stains.

A source of ions for electrophoretic transfer provided in the anodic gel matrix can be from a salt, acid, base, or buffer. Preferably, the body of anodic gel matrix comprises at least one buffer, preferably an organic buffer. A buffer provided in the anodic gel matrix can be a zwitterionic buffer. In preferred embodiments in which an analysis gel comprises proteins or peptide to be electroblotted, the body of anodic gel matrix comprises a buffer having a pKa of between about 6 and about 8, and more preferably between about 6.2 and about 7.2. A buffer can be present at a concentration of from about 10 mM to about 1 M, for example, at a concentration of between about 20 mM and about 500 mM, and in some embodiments between about 50 mM and about 300 mM.

For example, the body of anodic gel matrix can comprise 2-(N-morpholino)-ethanesulfonic acid (MES), N-(2-acetamido)-2-aminoethanesulfonic acid (ACES), piperazine-N, N'-2-ethanesulfonic acid (PIPES), 2-(N-morpholino)-2-hydroxypropane-sulfonic acid (MOPSO), N,N-bis-(hydroxyethyl)-2-aminoethanesulfonic acid (BES), 3-(N-morpholino)-propanesulfonic acid (MOPS), N-tris-(hydroxymethyl)-2-ethanesulfonic acid (TES), N-2-hydroxyethyl-piperazine-N-2-ethanesulfonic acid (HEPES), 3-(N-tris-(hydroxymethyl)methylamino)-2-hydroxypropanesulfonic acid (TAPSO), 3-(N,N-Bis[2-hydroxyethyl]amino)-2-hydroxypropanesulfonic acid (DIPSO), N-(2-Hydroxyethyl)-piperazine-N'-(2-hydroxypropanesulfonic acid) (HEPPSO), 4-(2-Hydroxyethyl)-1-piperazinepropanesulfonic acid (EPPS), N-[Tris(hydroxymethyl)methyl]-glycine (Tricine), N,N-Bis(2-hydroxyethyl)glycine (Bicine), (2-Hydroxy-1,1-bis-(hydroxymethyl)ethyl)amino]-1-propanesulfonic acid (TAPS), N-(1,1-Dimethyl-2-hydroxyethyl)-3-amino-2-hydroxypropanesulfonic acid (AMPSO), tris(hydroxy methyl)amino-methane (Tris), or bis[2-hydroxyethyl]iminotris[hydroxymethyl]methane (BisTris).

In some preferred embodiments of dry electroblotting systems of the invention, one or more buffers can be provided in the anodic gel matrix of an electroblotting system that is not provided in the cathodic gel matrix. In these embodiments, the blotting membrane is positioned on the anode side of the analysis gel.

Without limiting the invention to any particular mechanism, it is contemplated that one or more species of anions present in an anodic gel matrix of an electroblotting system that moves relatively fast when an electric field is established during electrophoretic transfer can, as it migrates rapidly to the anode, contribute to the electrophoretic concentration of migrating biomolecules which are also moving toward the anode, but are moving in a part of the field that lacks the fast-moving anions. In the context of electrophoretic transfer, biomolecules that are migrating "behind" fast moving anions (that is, they are farther from the anode) experience an electrophoretic concentration that is amplified by the depletion of the fast-moving ions from the anodic gel matrix as the fast-moving anions rapidly move to the anode. When the concentrated transferring biomolecules contact the blotting membrane, they are likely to become so concentrated as a result of this force as to be at least partially de-solubilized and potentially aggregated on the surface of the membrane that faces the gel. In denaturing gels, the sodium dodecyl sulfate (SDS) used to solubilize the proteins also migrates faster than the proteins, and is thus likely to be largely stripped from the proteins when they contact the blotting membrane. The de-solubilization of the transferred biomolecules at the surface of the blotting membrane inhibits their further migration and thus, in effect "stacks" the biomolecules on the membrane surface. This stacking effect can improve detection of biomolecules on blotting membranes.

The effect of anionic compounds provided exclusively in the anodic gel matrix also applies to anionic compounds that are present at a significantly reduced concentration in the cathodic gel matrix when compared with the anodic gel matrix. As used herein "significantly reduced concentration" means that the concentration of the anionic buffer compound in the cathodic matrix is 0.5× or less, preferably 0.2× or less, and more preferably 0.1× or less when compared with the concentration of the anionic compound in the anodic gel matrix of an electroblotting system or apparatus. Thus, in one embodiment, the cathode compartment and the anode compartment of an electroblotting system can include the same anionic compound, in which the compound is present at different concentrations in the cathode compartment and the anode compartment.

Compounds provided in an anodic gel matrix of an electroblotting apparatus, device or system that are not present, or present in significantly reduced amounts, in the cathodic gel matrix, are buffer compounds that during electrophoretic transfer are present in the electroblotting system in the form of anions, and are referred to herein as "anionic buffer compounds". Anionic buffer compounds provided in the anodic gel matrix and not provided in the cathodic gel matrix (or provided in significantly reduced amount in the cathodic gel matrix) are "fast-moving" with respect to some other buffer compounds, including, for example, other anionic buffer compounds that may be provided in the cathodic gel matrix. Therefore the choice of anionic buffer compounds for preferential use in the anodic gel matrix will depend, in part, on the anionic compounds (such as buffers) provided in the cathodic gel matrix, the pH of the buffers in the anodic gel matrix and cathodic gel matrix, and the pKas of the anionic buffer compounds. For example, anionic buffer compounds that can be preferentially provided in the anodic gel matrix of an electrophoretic transfer system in which electroblotting occurs near neutral pH include compounds that have a pKa at or neutrality (between about pH 6 and about pH 8), in some examples between pH 6.0 and pH 8.0, and at least 0.5 log units below, such as, for example, about one log unit below, the pKa of one or more buffer compounds provided in the cathodic gel matrix.

In some embodiments, the anodic gel matrix of an electroblotting system includes an anionic buffer compound that is not present in the cathodic gel matrix, in which the anionic compound has a pKa near or below neutrality and is present as an anion at or near neutral pH. In some embodiments, the compound can be a biological buffer having a pKa of less that about 7.5, and preferably less than about 7.2, and in some embodiments below about 7.0, where the biological buffer compound forms an anion in solution during electrophoresis. In certain illustrative aspects, the anionic buffer has a pKa less than 7.5, 7.4, 7.3, 7.2, 7.1, 7.0, 6.9, 6.8, 6.7, 6.6, or 6.5.

Nonlimiting examples of anionic compounds that can be present in the anodic gel matrix and not present in the cathodic gel matrix include EDTA, succinate, citrate, aspartic acid, glutamic acid, maleate, cacodylate, N-tris-(hydroxymethyl)-2-ethanesulfonic acid (TES), 2-(N-morpholino)-ethanesulfonic acid (MES), N-(2-Acetamido)iminodiacetic acid (ADA), N-(2-acetamido)-2-aminoethanesulfonic acid (ACES), piperazine-N,N'-2-ethanesulfonic acid (PIPES), 2-(N-morpholino)-2-hydroxypropanesulfonic acid (MOPSO), N,N-bis-(hydroxyethyl)-2-aminoethanesulfonic acid (BES), or 3-(N-morpholino)-propanesulfonic acid (MOPS). Such anionic buffer compounds can be used in electroblotting systems in which the pKa of an anionic compound in the cathode compartment is greater than that of the anionic compound in the anode compartment. In these embodiments the cathode compartment of the system can include, for example, one or more of, glycine, N-2-hydroxyethyl-piperazine-N-2-ethanesulfonic acid (HEPES), 3-(N-tris-(hydroxymethyl)methylamino)-2-hydroxypropanesulfonic acid (TAPSO), 3-(N,N-Bis[2-hydroxyethyl]amino)-2-hydroxypropanesulfonic acid (DIPSO), N-(2-Hydroxyethyl)piperazine-N'-(2-hydroxypropanesulfonic acid) (HEPPSO), 4-(2-Hydroxyethyl)-1-piperazine propanesulfonic acid (EPPS), N-[Tris(hydroxymethyl)methyl]glycine (Tricine), N,N-Bis(2-hydroxyethyl)glycine (Bicine), [(2-Hydroxy-1,1-bis(hydroxymethyl)ethyl)amino]-1-propanesulfonic acid (TAPS), and N-(1,1-Dimethyl-2-hydroxyethyl)-3-amino-2-hydroxypropanesulfonic acid (AMPSO).

In some embodiments, an anionic compound present in an anodic gel matrix that is not present (or is present at significantly reduced concentration) in a cathodic gel matrix is a zwitterionic buffer with a pKa near or below neutrality, such as, for example, MES, MOPSO, BES, MOPS, or ACES. Electroblotting systems that include one or more of these buffers in the anodic gel matrix can optionally comprise a zwitterionic buffer with a pKa near or above neutrality in the cathode compartment, such as, for example, Tricine, Bicine, TAPS, TAPSO, or AMPSO.

An anion-forming buffer compound present in an anodic gel matrix of an electroblotter and absent from (or present in significantly reduced amounts in) the cathodic gel matrix of an electroblotter can be present at any concentration, but preferably is present in the anodic gel matrix at a concentration of at least 10 millimolar, more preferably at a concentration of about 10 millimolar to about 1 Molar, more preferably yet from about 20 millimolar to about 500 millimolar, and in some embodiments from about 50 millimolar to about 300 millimolar.

The invention also includes wet and semi-dry electroblotting systems in which the anode compartment comprises an anionic buffer compound that is not present, or present at significantly reduced amounts, in the cathode compartment. In one embodiment, the anode compartment includes an anionic buffer compound that is not present in the cathode compartment, in which the compound has a pKa near or below neutrality and forms an anion at or near neutral pH. For example, the compound can be a biological buffer having a pKa of less that about 7.5, and preferably less than about 7.2, where the biological buffer compound forms an anion in solution during electrophoresis.

The anodic gel matrix body can further include ethylene glycol, an alcohol, one or more detergents (such as, for example, SDS) anti-fungal agents, blocking agents, anti-corrosion agents, modifying agents or enzymes, proteases, reducing agents, etc. The body of anodic gel matrix can comprise a dye, such as, for example, a positively charged nucleic acid or protein stain, including, for example, copper and silver.

In the dry electroblotting systems of the invention, the anodic body of gel matrix has first side that is in contact with one side the transfer stack and the cathodic body of gel matrix has a first side that is in contact with the opposite side of the transfer stack. In preferred embodiments, the first side of the body of anodic gel matrix that contacts one side the transfer stack and the first side of the body of cathodic gel matrix that contacts the other side of the transfer stack have length and width dimensions that conform closely to the length and width dimensions of the transfer stack blotting membrane and analysis gel. Preferably, to promote even-transfer of biomolecules from the gel to the blotting membrane, the length and width dimensions of the first side of the body of anodic gel matrix and the first side of the body of cathodic gel matrix are within 20% of the length and width dimensions of the transfer stack, more preferably within 10% of the length and width dimensions of the transfer stack, such as within 5% of the length and width dimensions of the transfer stack, within 2% of the length and width dimensions of the transfer stack.

In preferred embodiments, the area of the side of the anodic gel matrix that contacts the gel stack is the same as the area of the surface of gel stack in contact with the anodic gel matrix. In preferred embodiments, the area of the side of the cathodic gel matrix that contacts the gel stack is the same as the area of the surface of gel stack in contact with the cathodic gel matrix.

In a dry electroblotting system of the invention, the anodic body of gel matrix is in contact with the anode. In some preferred embodiments, the anode is attached to or juxtaposed with a second side of the anodic body of gel matrix, where the second side of the anodic body of gel matrix is opposite the first side of the anodic body of gel matrix that is in contact with the transfer stack. The anode can comprise any appropriate conductive material, and can be of any shape, for example, the anode can be a layer that includes a non-metallic electrically conducting material, a coil structure, a mesh comprising a non-metallic electrically conducting material, a metal foil, a metal mesh and/or combinations thereof. In certain embodiments, an electrically conducting electrode can comprise a nonconducting polymer coated with a conducting metal or nonmetal. An electrode of a nonconducting material coated with a conducting material can be in the form of a sheet, mesh, or other structure. An electrode can also comprise one or more electrically conducting non-metallic materials such as graphite, carbon, an electrically conducting polymer, and or any combinations thereof. The anode can comprise, for example, a conducting polymer, platinum, stainless steel, carbon, graphite, aluminum, copper, silver, or lead. In some embodiments, the anode comprises an electrochemically ionizable metal, such as, for example, copper, silver, or lead. The use of an electrochemically ionizable metal anode allows electrophoretic transfer to occur in the absence of oxygen evolution at the anode, as copper metal is preferentially ionized in place of water. This avoids the formation of bubbles that can interfere with electrophoretic transfer. In some preferred embodiments, the anode is a disposable copper electrode. In other embodiments, the anode can comprise aluminum, which absorbs oxygen gas. In some preferred embodiments, the anode is a disposable aluminum electrode.

An electrode can comprise copper coated with silver, or another metal or material that is coated with silver. For example, it may be possible to use a carbon or graphite based electrically conducting electrode and coat it with a suitable silver metal paste or emulsion or to apply silver to the material of the electrode using any other suitable method known in the art. A silver-coated anode, for example, can release silver ions that migrate toward the blotting membrane and stain biomolecules such as nucleic acids or proteins, as provided in Example 4.

It is also possible, in accordance with another embodiment of the invention, to deposit or coat silver metal (using various different metal deposition methods) on an electrically conducting substrate (such as, but not limited to a copper mesh or grid or a carbon or graphite based fabric, or even a thin layer of an electrically conducting polymer). The methods that may be used to apply a silver metal coating to such electrically conducting electrodes may include, inter alia, chemical vapor deposition (CVD) methods, silver coating by dipping the electrode in molten silver, electroplating methods, methods of spray coating using silver particles dispersed in a suitable adhesion enhancing composition or formulation, chemical deposition methods performed in an aqueous or non-aqueous solutions (such as, for example, immersing the conductive electrode in an ammoniacal silver nitrate solution including glucose, as is well known in the art of silver coated mirror forming), direct vacuum deposition of silver from a hot silver metal filament onto a target electrode, and the like. Thus, any suitable silver coating or deposition or application methods known in the art may be used in obtaining the silver metal coated electrode of the present invention.

In a dry electroblotting system of the invention, the cathodic body of gel matrix is in contact with the cathode. In some preferred embodiments, the cathode is attached to or juxtaposed with a second side of the cathodic body of gel matrix, where the second side of the cathodic body of gel matrix is opposite the first side of the cathodic body of gel matrix that is in contact with the transfer stack. The cathode can comprise any appropriate conductive material, and can be of any shape, for example, the cathode can be a layer that includes a non-metallic electrically conducting material, a mesh comprising a non-metallic electrically conducting material, a metal foil, a metal mesh and/or combinations thereof. In certain embodiments, an electrically conducting electrode can comprise a nonconducting polymer coated with a conducting metal or nonmetal. An electrode of a nonconducting material coated with a conducting material can be in the form of a sheet, mesh, or other structure. An electrode can also comprise one or more electrically conducting non-metallic materials such as graphite, carbon, an electrically conducting polymer, and or any combinations thereof. The cathode can comprise, for example, a conducting polymer, platinum, stainless steel, carbon, graphite, aluminum, copper, silver, or lead. In some preferred embodiments, the cathode is a disposable copper electrode. In other embodiments, the cathode can comprise palladium, which absorbs hydrogen gas produced at the cathode during electrophoretic transfer. In some preferred embodiments, the cathode is a disposable aluminum electrode.

In preferred embodiments, the anode and cathode have the same or similar length and width dimensions as the anodic body of gel matrix and cathodic body of gel matrix, respectively. The surface of an anode or cathode that is juxtaposed with a body of gel matrix need not be continuous; for example, an electrode can be a wire mesh or coil structure. In such embodiments, the surface of an electrode in contact with a gel matrix is considered to be defined by the outer dimensions of the surface of the electrode structure that is juxtaposed with the gel matrix. Preferably, the anode surface juxtaposed with an anodic body of gel matrix contacts at least 50%, at least 60%, more preferably at least 70%, at least 80%, at least 90%, or at least 95% of the side of the anodic gel matrix it is juxtaposed with. The anode surface juxtaposed with an anodic body of gel matrix can have an area that is essentially the same as the surface area of the side of the anodic gel matrix it is juxtaposed with. For example, for a generally rectangular, oval, or round electrode and body of gel matrix, the length and width dimensions of the anode are preferably within 20% of the length and width dimensions of the body of anodic gel matrix, more preferably within 10% of the length and width dimensions of the body of anodic gel matrix, such as within 5% of the length and width dimensions of the body of anodic gel matrix, within 2% of the length and width dimensions of the body of anodic gel matrix. In these preferred embodiments, it is also preferred that the anodic body of gel matrix conforms closely to the length and width dimensions of the transfer stack blotting membrane and analysis gel.

Preferably, the cathode surface juxtaposed with an cathodic body of gel matrix contacts at least 50%, at least 60%, more preferably at least 70%, at least 80%, at least 90%, or at least 95% of the side of the cathodic gel matrix it is juxtaposed with. The cathode surface juxtaposed with an cathodic body of gel matrix can have an area that is essentially the same as the surface area of the side of the cathodic gel matrix it is juxtaposed with. For example, for a generally rectangular, oval, or round electrode and body of gel matrix, the length and width dimensions of the cathode are preferably within 20% of the length and width dimensions of the body of cathodic gel matrix, more preferably within 10% of the length and width dimensions of the body of cathodic gel matrix, such as within 5% of the length and width dimensions of the body of cathodic gel matrix, within 2% of the length and width dimensions of the body of cathodic gel matrix. In these preferred embodiments, it is also preferred that the cathodic body of gel matrix conforms closely to the length and width dimensions of the transfer stack blotting membrane and analysis gel.

Thus, in preferred embodiments the invention provides a system having an anode in contact with an anodic body of gel matrix which is in contact with one side of a transfer stack, and a cathode in contact with an cathodic body of gel matrix which is in contact with the opposite side of a transfer stack in which the anode, anodic body of gel matrix, cathode, cathodic body of gel matrix, and transfer stack have the same or nearly the same length and width dimensions.

In some embodiments, an anode, a cathode, or both is provided as an integral part (meaning it is not detached by the user after each transfer), of a power supply or apparatus that holds an electroblotting transfer stack. In other embodiments, the anode or cathode can be separate from a power supply or apparatus. For example, an electrode can be a disposable electrode provided as part of an electrode assembly or separate from the body of gel matrix. An electrode provided separately from a gel matrix can be attached to a dry electroblotting apparatus after which a body of gel matrix can be fitted to the apparatus such that it contacts the electrode, or both electrode and body of gel matrix can be positioned in a holder, such as a tray or cage, that can be attached to or fitted to an electroblotting apparatus.

In some embodiments, the anode, cathode, or both is provided as part of an electrode assembly attached to a body of gel matrix, for example, the anode or cathode can be attached using fasteners or holders that position the electrode against a body of gel matrix. In certain embodiments, an anode or cathode is at least partially embedded in the anodic body of gel matrix. For example, a body of gel matrix can be made by pouring or unsolidified gel components over an electrode or by using gel extrusion techniques, such that the electrode becomes partially coated or embedded on at least one side by gel matrix. In certain embodiments, the body of gel matrix is positioned against the conducting electrode in a plastic tray before and during electrophoretic transfer. The plastic tray preferably has at least one region that comprises conductive material for providing electrical connection between the electrode and an electrical contact of a power supply or source.

A dry electroblotting system can further include a power supply having electrical contacts for contacting the anode and cathode. The power supply can have a base for positioning a transfer stack during electrophoretic transfer. In some embodiments, an anode, a cathode, or both can be integral to a power supply of the system. In one embodiment, a cathode is integral to a power supply of the electroblotting system, and an anode is separate and disposable.

Electrode Assemblies for Dry Electroblotting

The invention provides electrode assemblies for performing dry electroblotting, in which an electrode assembly includes a body of gel matrix as described herein that includes a source of ions; and an electrically conducting electrode juxtaposed with the body of gel matrix.

A body of gel matrix juxtaposed with an electrode can have a composition as described previously herein, and can include suitable polymers such as but not limited to, agarose, acrylamide, alumina, silica, starch or other polysaccharides such as chitosan, gums (e.g., xantham gum, gellan gum), carrageenan, pectin, or any combinations of these.

As described herein for a body of gel matrix in a dry electroblotting system, a body of gel matrix of an electrode assembly comprises at least one source of ions. An ion source within the body of gel of an electrode assembly may be, for example, the buffers previously disclosed herein, or any suitable buffer solution incorporated in the body of gel such as, but not limited to, any buffer known in the art to be used for blotting, for example Tris Glycine (Tris 20-500 mM [more typically, 25 mM to 200 mM], Glycine 20-500 mM [more typically, 25 mM to 200 mM]), 0.2×-5× Tris acetate EDTA (typically 0.5×-2×), 0.2×-5× Tris borate EDTA (typically 0.5×-2×), CAPS buffer (5-200 mM, or mM to 100 mM), BisTris Bicine, (BisTris 5 mM-500 mM, or 20-100 mM, Bicine 5 mM to 500 mM, or 20-100 mM) or BisTris Tricine (BisTris 5 mM-500 mM, or 20-250 mM, Tricine 5 mM to 500 mM, or 20-250 mM), as well as MES, MOPS, or other buffers. All of the above described buffers may or may not include sodium dodecyl sulfate (SDS), the combination of BisTris, Tricine, BES and SDS or other detergents, and others. The gel body can further include ethylene glycol, an alcohol, one or more detergents, one or more anti-fungal agents, one or more anti-corrosion agents, one or more reducing agents, etc.

Another source of ions that can be present is an ion exchange matrix. The ion exchange matrix may be "loaded" with ions prior to being added to a gel solution for making a body of gel. An ion exchange matrix can be present in an electrode assembly gel matrix body intended for use as an anode assembly or cathode assembly. For example, in some embodiments the body of gel at the anode comprises an ion exchange matrix in the form of DE-52 (DEAE) cellulose that has been loaded with an anion such as Tricine.

The gel matrix of a cathode electrode assembly can further comprise one or more salts, acids, bases, buffers, dyes, reducing agents, blocking agents, chelators, inhibitors, cleavage reagents, modifying enzymes or reagents, or solubilizing agents that is not present in the anode electrode assembly gel matrix. The anodic gel matrix can further comprise one or more salts, buffers, dyes, reducing agents, chelators, inhibitors, cleavage reagents, modifying enzymes or reagents, or solubilizing agents that is not present in the cathodic gel matrix.

As described in the previous section on dry electroblotting systems, a gel matrix of an electrode assembly for use as an anode assembly can include one or more buffer compounds that are not present, or present in significantly reduced amounts, in the cathodic gel matrix. Such buffer compounds are preferably anionic buffer compounds, and as described previously herein, can include without limitation, EDTA, succinate, citrate, aspartic acid, glutamic acid, maleate, cacodylate, TES, MES, ADA, ACES, PIPES, MOPSO, BES, or MOPS.

A body of gel matrix of an electrode assembly will typically have two opposing sides, one of which contacts the electrode, and the other of which directly or indirectly contacts the transfer stack. An electrode "juxtaposed with" a body of gel matrix is in contact with the body of gel, and preferably is aligned along a side of the body of gel matrix with which it is in continuous contact. In certain embodiments, the juxtaposed conducting electrode is attached to the body of gel matrix. The attachment can be physical, for example, by means of gravity or a holder that maintains the electrode and body of gel matrix in close apposition, or can be chemical. Chemical attachments can be covalent or noncovalent. For example, an electrode can be attached to the body of gel by electrostatic interaction. In certain embodiments, the electrically conducting electrode juxtaposed with a body of gel is at least partially embedded in the body of gel.

An electrically conducting electrode used in the electrode assemblies provided herein can be, for example, a layer that includes a non-metallic electrically conducting material, a mesh comprising a non-metallic electrically conducting material, a metal foil, a metal mesh and/or combinations thereof. In certain embodiments, an electrically conducting electrode can comprise a nonconducting polymer coated with a conducting metal or nonmetal. An electrode of a nonconducting material coated with a conducting material can be in the form of a sheet, mesh, or other structure. An electrode can also comprise one or more electrically conducting non-metallic materials such as graphite, carbon, an electrically conducting polymer, and or any combinations thereof.

In certain embodiments, an electrically conducting electrode of an electrode assembly comprises an electrochemically ionizable metal such as lead, copper, silver or combinations thereof. When non-electrochemically ionizable metals are used as electrodes, electrolysis of water produces protons at the anode and hydroxyl ions at the cathode during electrophoresis. An electrochemically ionizable metal that ionizes during electrophoresis can produce metal ions when a potential difference is applied over the anode and cathode instead of, for example, protons at the anode. The use of an electrode of an electrochemically ionizable metal, in avoiding water electrolysis at the electrode, can also avoid the concomitant release of oxygen at the anode, thus avoiding the release of bubbles that can interfere with even electrophoretic transfer.

In some embodiments, of the invention, the anode comprises lead, copper or silver. In some embodiments, of the invention, the cathode comprises copper or silver. In some embodiments, of the invention, the anode comprises copper. In some embodiments, the anode comprises a copper sheet. In some embodiments, the anode comprises a copper mesh or a polymeric mesh that is coated with copper.

Other electrode materials include metals such as, without limitation, stainless steel or platinum, or aluminum or palladium. Aluminum can absorb oxygen gas, such as oxygen gas generated at the anode during electrophoretic transfer. Palladium can absorb hydrogen gas, such as hydrogen gas generated at the cathode during electrophoretic transfer.

One or more blotting membranes can optionally be part of an electrode assembly. In some embodiments, a membrane is included in the anode electrode assembly, in the membrane is juxtaposed on the side of the body of gel matrix opposite the side juxtaposed with the electrode, such that the blotting membrane will be positioned against the separating gel during electroblotting. It is also possible, however, to have a blotting membrane present in the cathode assembly, or in both the anode and cathode assemblies. A blotting membrane can be, for example, paper, a cellulose-based blotting membrane (such as but not limited to cellulose nitrate or cellulose acetate), a nitrocellulose-based membrane, a nylon-based membrane, or polyvinylidene difluoride (PVDF)-based membrane, or activated or derivatized versions of these (such as, for example, surface-charged derivatives).

In some embodiments, an anode assembly includes a tray, in which the tray holds an electrically conductive electrode, a body of gel matrix juxtaposed with the electrode, such that the electrode contacts a first side of the body of gel matrix, and, optionally, a blotting membrane juxtaposed with the body of gel matrix, such that the blotting membrane contacts a second side of the body of gel matrix that is opposite the first side of the gel matrix body. The tray is configured to fit a dry blotting apparatus, such that the electrode, body of gel matrix, and blotting membrane remain in the tray during electrophoretic transfer. In these embodiments, the tray of the anodic assembly comprises a metal contact strip or region that transmits current from the electrode in the tray to the electrical contact of the electroblotting apparatus.

Kits for Electroblotting

In yet another aspect, provided herein are kits for performing dry electroblotting. In one embodiment, a kit includes at least one body of gel matrix that comprises an ion source for electrophoresis and at least one blotting membrane. The body of gel matrix can have a composition as described herein, and preferably includes a buffer ion source. A body of gel matrix and a blotting membrane provided together in a kit can have length and width dimension that are the same or nearly the same, such as within 10%, within 5%, or within 2% of one another in length and width.

In another embodiment, a kit includes at least one body of anodic gel matrix and at least one body of cathodic gel matrix, in which the anodic gel matrix includes at least one anionic buffer compound not present, or present in significantly reduced amounts, in the cathodic gel matrix. As described in previous sections, the anionic buffer compound is preferably a buffer compound with a pKa at or near neutrality. Preferably, both the anode gel matrix and the cathodic gel matrix comprise buffer ion sources, and the cathode compartment includes a buffer compound that is not present (or present in significantly reduced amount) in the anode compartment, in which the cathode buffer compound has a pKa at least about 0.5 log units higher, such as about one log unit higher, than a buffer in the anodic compartment, in which the buffer forms an anion above neutral pH.

In another embodiment, a kit includes at least one body of anodic gel matrix and at least one body of cathodic gel matrix, in which the anodic gel matrix includes at least one dye, detergent, modifying enzyme or reagent, or reducing compound not present in the anodic gel matrix not present in the cathodic gel matrix. In another embodiment, a kit includes at least one body of anodic gel matrix and at least one body of cathodic gel matrix, in which the cathodic gel matrix includes at least one dye, detergent, modifying enzyme or reagent, or reducing compound not present in the anodic gel matrix. For example, a body of cathodic gel matrix can comprise a dye such as but not limited to a copper-based dye, a Direct Blue dye (Sigma Aldrich), a Coomassie dye, or a SYPRO dye. Either of both of a cathodic gel matrix or an anodic gel matrix can comprise an ion exchange matrix.

A body of anodic gel matrix and a body of cathodic gel matrix may be provided in a kit in sealed packages. Electroblotting gel matrix kits can also optionally further include at least one blotting membrane, at least one sheet of filter paper, at least one sponge, and/or at least one electrode. Blotting membranes can be provided juxtaposed with a body of gel matrix, or separately.

In another aspect, a kit of the invention provides one or more disposable anodic electrode assemblies and/or one or more disposable cathodic electrode assemblies. In some embodiments, one or more anodic electrode assemblies can include a body of gel including a source of ions and an electrode juxtaposed with a gel matrix. In some embodiments, one or more cathodic electrode assemblies can include a body of gel including a source of ions and an electrode juxtaposed with a gel matrix.

In preferred embodiments, an anode of an electrode assembly provided in a kit has a surface juxtaposed with an anodic body of gel matrix that contacts at least 50%, at least 60%, more preferably at least 70%, at least 80%, or at least 90% of the side of the anodic gel matrix it is juxtaposed with. In preferred embodiments, an anode of an electrode assembly provided in a kit has a surface juxtaposed with an anodic body of gel matrix that has length and width dimensions that are within 20%, within 10%, within 5%, or within 2% of the length and width dimensions of the side anodic body of gel matrix it is juxtaposed with. In exemplary embodiments, the anode and anodic body of gel matrix are generally rectangular.

In preferred embodiments, a cathode of an electrode assembly provided in a kit has a surface juxtaposed with an cathodic body of gel matrix that contacts at least 50%, at least 60%, more preferably at least 70%, at least 80%, or at least 90% of the side of the cathodic gel matrix it is juxtaposed with. In preferred embodiments, an cathode of an electrode assembly provided in a kit has a surface juxtaposed with an cathodic body of gel matrix that has length and width dimensions that are within 20%, within 10%, within 5%, or within 2% of the length and width dimensions of the side cathodic body of gel matrix it is juxtaposed with. In exemplary embodiments, the cathode and cathodic body of gel matrix are generally rectangular.

An anodic electrode assembly and/or a cathodic electrode assembly can be provided in a tray, such as a plastic tray. An anodic electrode assembly provided in a kit can optionally include one or more blotting membranes juxtaposed with a second side of the body of gel matrix.

The anodic and/or cathodic electrode assemblies can be enclosed within a sealed package together, or separately. Furthermore, multiple anodic and/or cathodic electrode assemblies can be enclosed together in packaging.

In some aspects, an electroblotting kit includes one or more disposable anodic electrode assemblies and one or more disposable cathodic electrode assemblies. In some aspects, an electroblotting kit includes one or more disposable anodic electrode assemblies and at least one body of cathodic gel matrix. The kits can optionally include one or more blotting membranes, sheets of filter paper, or sponges.

Electrodes can also be provided separately in kits. One or more electrodes can be provided, for example, in a sealed container that also includes a dessicant or an anti-corrosive agent. The electrodes can be packaged in liquid or gel, such as an alcohol or a solution or gel comprising one or more preservatives, reducing agents, or anti-corrosives. Kits providing electrodes, such as disposable electrodes, can also include one or more gel matrices, one or more blotting membranes, or one or more sheets of filter paper.

The anodic and/or the cathodic electrode assemblies of the kit may be individually wrapped in a suitable gas and water impermeable wrapper (or any other type of suitable container), as is known in the art, in order to enable storage of the electrode assemblies for extended periods of time without drying. For example, the wrapper or container may be made from a suitable thin, water and gas impermeable plastic or polymer based sheet or foil, and may be sealed after packaging of the electrode therein using any suitable wrapper sealing method known in the art (such as, but not limited to gluing or contact heat sealing, or the like). Blotting membranes, when provided in kits, can be provided in separate wrapping, or together within a package that includes an electrode assembly.

Thus it will be appreciated by those skilled in the art that various different combinations and sub-combinations of the various different electrode assemblies disclosed hereinabove may be combined to form many different types of kits. Such kits may or may not include different stains as is known in the art and/or stain releasing metals (such as, for example anodic silver metal containing electrode assemblies, as disclosed hereinabove, depending on the application. Similarly the gel concentrations and compositions and the degree of cross linking may be varied to in accordance with the blotted species.

Furthermore, the dimensions of the various possible kit parts such as the different types of electrode assemblies and/or blotting membranes may be modified or adapted for use with the particular dimensions of the gel to be blotted.

It is also possible to include in such wrappers a suitable shallow open tray (not shown) made of plastic or other suitable material. The tray may have dimensions suitable for receiving the electrode assembly therewithin to protect the electrode assembly from mechanical damage during handling and to facilitate the handling and manipulation of the electrode assembly after the wrapper is opened before use. A tray that holds an electrode assembly can also be sealed over the top with fluid-impermeable plastic or foil (or foil-backed plastic), and the top sheet of plastic or foil can be removed to expose the electrode assembly for use. An electrode assembly (such as, for example, a cathode assembly) can be removed from the tray for use, or the electrode assembly can remain positioned within the tray during electroblotting.

The holding tray may be a rectangular tray to accommodate the shape of a rectangular electrode assembly. However, the holding tray may be made in other suitable shapes, depending, inter alia, on the shape of the electrode assembly (which in turn may vary in shape depending, inter alia, on the application). The holding tray may preferably be made from an inexpensive rigid or semi-rigid plastic or polymer such as, but not limited to, polyvinylchloride (PVC). It is, however, noted that any other suitable material(s) may be used for forming the holding tray.

In some embodiments a holding tray has a pulling tab on one side. The pulling tab may be formed as an integral part of the holding tray, but may also be formed as a separate piece (not shown) and attached to the holding tray by gluing or bonding, soldering or by any other suitable attaching method known in the art. The holding tray may also function as a stabilizer in the process of forming the blotting assembly prior to performing the electro-blotting transfer.

Figure 7:
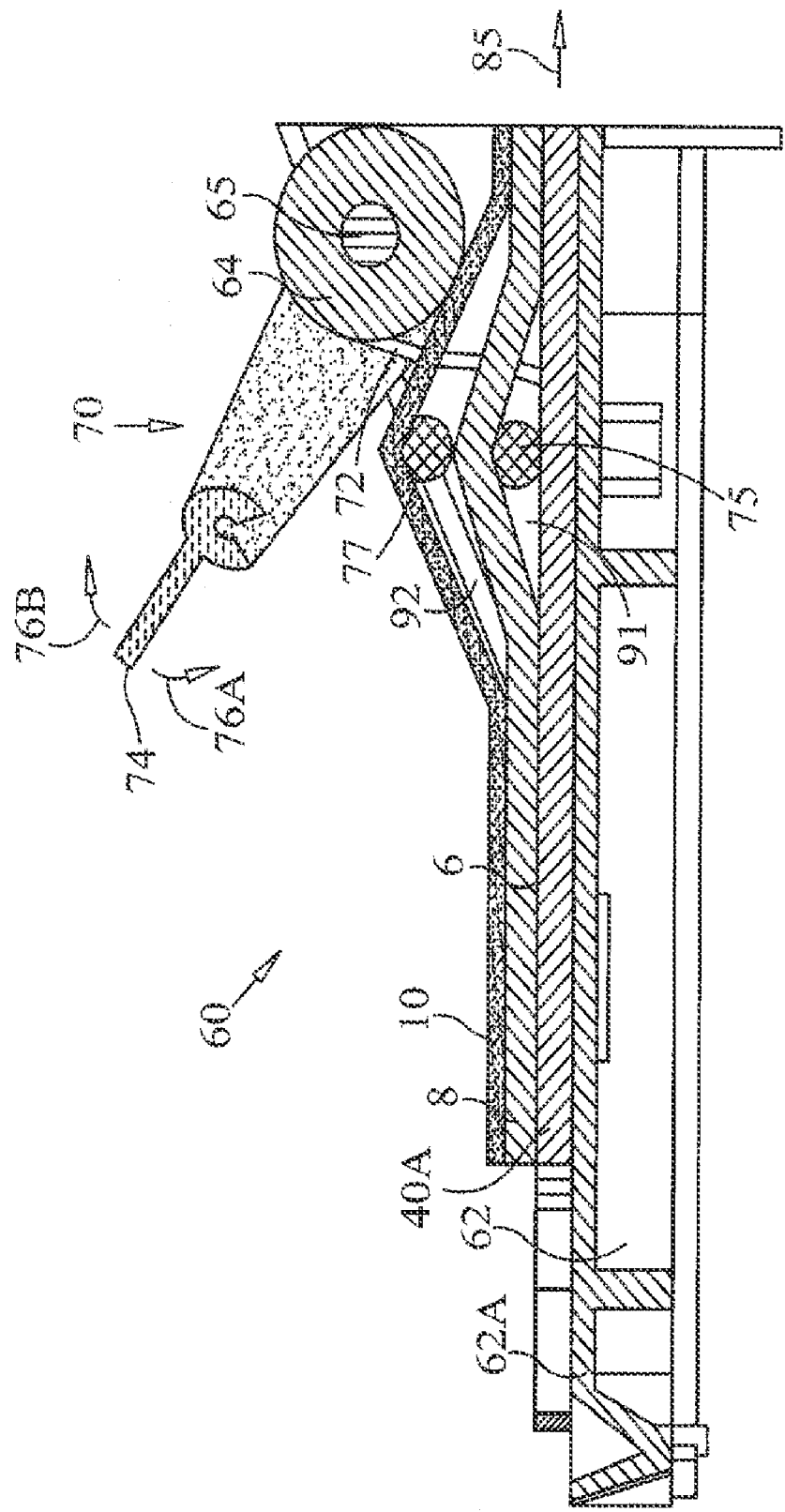
FIG. 7 is a schematic cross-sectional view of part of a de-bubbling device usable in reducing the trapping of air bubbles while attaching the dry electro-blotting electrode assemblies of the present invention to a gel to be electro-blotted in accordance with an embodiment of the present invention.

For example, when using the de-bubbling device 60 of FIG. 7, the wrapper may be opened and the holding tray may be taken out, or a plastic or foil top sheet sealing the tray, which also serves as the container for the electrode assembly, can be peeled off. The tray can be placed (together with the anodic electrode assembly included therewithin) on the surface 62A of the de-bubbler device 60. A gel (not shown) and a cathodic electrode assembly (not shown) may then be juxtaposed with the anodic electrode assembly 130 as described hereinabove in detail by using the separating members 75 and 77 and the roller 64. The pulling tab 223 may then be advantageously used for pulling the formed blotting assembly in the direction indicated by the arrow 85 of FIG. 7.

It is noted that after a blotting assembly (not shown) is formed using the de-bubbler device 60, the blotting assembly included in the holding tray 222 may be removed, the blotting assembly may then be taken out of the holding tray and positioned in the electro-blotting device 80 of the apparatus 100, as described in detail hereinabove for the blotting assembly 50 of FIG. 6.

Alternatively, in accordance with another embodiment of the present invention, the holding tray may be formed with an internal electrically conducting strip or segment for enabling the electroblotting procedure without removing the blotting assembly from the holding tray.

In another embodiment, provided herein is a method for generating revenue, that includes selling a disposable ion reservoir or a disposable electrode assembly for electro-blotting. The disposable ion reservoir is in the form of a body of gel matrix including a source of ions. An electrode assembly includes a body of gel matrix including a source of ions and an electrically conducting electrode juxtaposed with said body of gel. The body of gel can further include a staining compound embedded therein. The disposable electrode assembly is sold by a provider to a customer using, for example, a phone-based order system, or an on-line Internet order system.

Dry Blotting Apparatus

The invention in some aspects provides an apparatus for dry blotting gels, in which the apparatus includes: a power supply; a first surface for positioning an anode assembly, in which the surface includes an electrical contact for connecting to an anode of an anode assembly; a second surface that includes an electrical contact for connecting to a cathode of a cathode assembly; in which the first and second surfaces of the apparatus can be positioned to hold an anode assembly, a cathode assembly, and a gel between the anode and cathode assemblies; in which the apparatus does not include, hold, or connect to reservoirs for holding liquid buffers for electrophoretic transfer. In some aspects, the invention provides an electroblotting system that includes an apparatus for dry electroblotting as provided, and further includes an anode assembly and a cathode assembly. The anode assembly includes an anode, an anodic body of gel matrix that includes at least one ion source, and a membrane. The cathode assembly comprises a cathode and a cathodic body of gel matrix that includes at least one ion source. In some embodiments, the dry electroblotting apparatus comprises software that includes a menu of electroblotting conditions. In some embodiments, the dry electroblotting apparatus comprises an AC/DC electrical adaptor. In some embodiments, the dry electroblotting apparatus comprises at least one universal serial bus (USB) port.

Methods of Performing Dry Electroblotting

In another aspect, provided herein is a method for performing dry electroblotting, that includes positioning a transfer stack that includes an analysis gel that comprises one or more biomolecules and at least one blotting membrane between an anode assembly and a cathode assembly, and passing an electric current between the anode of the anode assembly and the cathode of the cathode assembly to transfer one or more biomolecules from the analysis gel to a blotting membrane.

An analysis gel used in the methods of the invention has a first face and a second face, in which a first face of the analysis gel is juxtaposed with a blotting membrane, and the second face of the analysis gel is positioned in direct or indirect contact with an electrode assembly. In some embodiments, the second face of the analysis gel is in contact with a cathodic electrode assembly. If the contact between the gel and the cathodic electrode assembly is indirect (for example, wetted filter paper may be between the cathodic gel matrix and an analysis gel), the indirect contact provides electrical continuity between the analysis gel and the cathodic gel matrix. The stack is positioned such that the blotting membrane is in direct or indirect contact with the anodic gel matrix. If the contact between the blotting membrane and the anodic electrode assembly is indirect (for example, wetted filter paper may be between the anodic gel matrix and an analysis gel), the indirect contact provides electrical continuity between the analysis gel and the anodic gel matrix.

In certain illustrative aspects of the method, the anodic electrode is made of copper. In certain illustrative aspects, both the anodic and cathodic electrodes are made of copper. In some aspects, current density used to pass a current can be equal to or larger than 15 milliamperes per square centimeter of the first surface of said separating gel. The invention includes a method that includes transferring biomolecules, such as proteins from a separating gel, to a blotting membrane using a copper electrode. The use of copper metal in the anodic electrode assemblies of the present invention substantially reduces or eliminates the release of gas and formation of bubbles between the electrically conducting copper electrode and the attached body of gel and therefore enables the use of larger currents leading advantageously to a faster blotting time.

For example, in illustrative electroblotting methods of the present invention, current densities used for electroblotting are between about 10 and 50 milliamperes per square centimeter (10-50 mA/cm$^2$). The invention includes an electroblotting method comprising transferring biomolecules such as proteins from a separating gel to a blotting membrane using a current of between 10 and 50 mA/cm$^2$. In certain aspects, electroblotting is performed between 20 and 40 mA/cm$^2$, and in illustrative examples, the electroblotting is performed at between 25 and 35 mA/cm$^2$. In other aspects, the method is performed at currents of greater than 10, 15, 20, 25, or 30 mA/cm$^2$.

The use of higher current densities advantageously allows the shortening of the time required for blotting, and therefore saves time and allows the performance of more blotting procedures per each blotting apparatus in a given time period. Accordingly, provided herein is a method for electroblotting that includes transferring one or more populations of structurally identical biomolecules such as one or more populations of proteins, from a separating gel to a blotting membrane, wherein at least 50% of a population of structurally identical biomolecules are transferred from the separating gel to the blotting membrane in less than 15, 10, 9, 8, 7, 6, or 5 minutes. The biomolecule can be, for example, a protein of at least 10, 15, 20, 30, 40, 50, 60, 70, 75, 90, or 100 kDa. In certain illustrative embodiments, at least 50% of a population of 50 kDa proteins are transferred from a separating gel to a blotting membrane in 15, 10, 8, 7, or 6 minutes or less.

In some preferred embodiments, a gel is equilibrated in a buffer or solution prior to electroblotting. For example, a gel can be incubated for 10 min to 1 hour, for example, for about 20 minutes, in 20% ethylene glycol/1× NuPAGE transfer buffer (Invitrogen), 100 mM BisTris, 75 mM Tricine, 100 mM BisTris, 75 mM Tricine plus 20% ethylene glycol, or 10% methanol in 2× NuPAGE Transfer Buffer (Invitrogen) with a 1:1000 dilution of Anti-oxidant (Invitrogen).

In some embodiments the transfer stack is positioned between an anodic electrode assembly that includes an anodic body of gel matrix and an anodic electrode juxtaposed with a first side of the anodic body of gel and a cathodic electrode assembly that includes a cathodic body of gel matrix and a cathodic electrode juxtaposed with a first side of the cathodic body of gel. In some aspects, the blotting membrane is provided with the anodic electrode assembly.

The present invention also includes methods of transferring one or more biomolecules to a membrane, in which the one or more biomolecules are transferred to membranes using an electroblotting system that includes a power supply, an anode, an anode compartment that includes a source of ions for electrophoretic transfer, a cathode, a cathodic compartment that includes a source of ions for electrophoretic transfer, an electrophoresis gel, and a blotting membrane, in which the anode compartment includes at least one compound that is present as an anion under electrophoretic conditions, where the compound is not present in the cathode compartment, or is present in the cathode compartment at significantly reduced concentration. The compound that is present in the anode compartment and not present in the cathode compartment is preferably a buffer compound having a pKa near or below neutrality, such as a pKa below about 7.5, preferably below about 7.2, and more preferably at or below about 7. In some embodiments, the buffer compound with a pKa near or below neutrality is a zwitterionic buffer.

The present invention thus includes methods of detecting one or more biomolecules, in which the one or more biomolecules are transferred to membranes using an electroblotting system that includes a power supply, an anode, an anode compartment that includes a source of ions for electrophoretic transfer, a cathode, a cathodic compartment that includes a source of ions for electrophoretic transfer, an electrophoresis gel, and a blotting membrane, in which the anode compartment includes at least one compound that is present as an anion under electrophoretic conditions, where the compound is not present in the cathode compartment, or is present in the cathode compartment at significantly reduced concentration. The method further includes detecting one or more biomolecules transferred to the membrane using one or more of protein staining or immunodetection. Immunodetection can include one or more of chemiluminescence detection, chromogenic substrate detection, radioisotope detection, or fluorescence detection, as known in the art and described herein.

As shown in Examples 13 and 14, detection of biomolecules such as proteins on membranes can be improved when the proteins are electroblotted to the membranes using an apparatus and system of the present invention, when compared with the detection of proteins electroblotted using conventional wet or semi-dry electroblotting. For example, detection can be enhanced, about 2-fold, about 4-fold, or greater using a dry electroblotting system of the invention.

In some aspects, a cathode compartment of an electroblotting system can comprise one or more compounds not present in the anode compartment. For example, a cathode compartment can include one or more buffer compound that is not present, or present in significantly reduced amount, in the anode compartment. In one embodiment the cathode compartment includes a buffer compound that is not present (or present in significantly reduced amount) in the anode compartment, in which the compound has a pKa at least about 0.5 log units higher, such as about one log unit higher, than a buffer in the anodic compartment, in which the buffer forms an anion above neutral pH. For example, the compound can be a biological buffer having a pKa of greater that about 7.5, and preferably of greater than 7.5, such as 8 or above.

Nonlimiting examples of buffer compounds that can be present in the anodic gel matrix and not present in the cathodic gel matrix include glycine, borate, TES, HEPES, TAPSO, DIPSO, HEPPSO, EPPS, Tricine, Bicine, TAPS, AMPSO. In some embodiments, a buffer compound present in a cathode compartment that is not present in an anode compartment is a zwitterionic buffer with a pKa near or above neutrality, such as, for example, glycine, HEPES, DIPSO, HEPPSO, EPPS Tricine, Bicine, TAPS, TAPSO, or AMPSO.

An anion-forming buffer compound present in the cathode compartment can be present at any concentration, but preferably is present at a concentration of at least 10 millimolar, more preferably at a concentration of about 10 millimolar to about 1 Molar, more preferably yet from about 20 millimolar to about 500 millimolar.

In these aspects of the invention, the preferential use of particular buffers, such as but not limited to anionic buffers, in the cathode compartment, will depend on the anionic compounds provided in the anode compartment. In some embodiments, anode-cathode compartment buffer combinations are selected to provide at least one anionic buffer in the anode compartment that is either not present, or present in significantly reduced concentration, in the cathode compartment, and at least one anionic buffer in the cathode compartment that has a pKa at least 0.5 log units higher, such as about one log unit higher, than that of the anionic buffer preferentially provided in the anode compartment. The anionic buffer in the cathode compartment can also be present in the anode compartment, at the same or different concentration. In some embodiments, at least one buffer provided in the anode compartment that is either not present, or present in significantly reduced concentration, in the cathode compartment, is a zwitterionic buffer. In some embodiments, at least one buffer provided in the cathode compartment is a zwitterionic buffer that has a pKa higher than that of the anionic buffer preferentially provided in the anode compartment.

Those skilled in the art will recognize that the choice of components differentially provided in the anode or cathode will depend, in part, on the pH at which the electrotransfer occurs, which determines the ionization state of the compounds. While the compounds referred to herein have pKa's ranging from about 6 to about 8, it is of course possible to select compounds within or outside this range to optimize the transfer effects depending on the transfer conditions, and in particular the pH range at which transfer occurs.

These aspects of the invention that include methods and compositions for increasing the sensitivity of detecting a biomolecule that has been electrophoretically transferred are not limited to dry electroblotting methods and composition. For example, the inclusion of compounds that produce fast-moving anions, such as those disclosed herein, on the anode side of an electrotransfer system or apparatus can be applied to wet and semi-dry electroblotting as well as dry electroblotting. For example, an anodic buffer reservoir can include a compound as disclosed herein, that when present on the anode side of a gel undergoing wet electroblotting, improves detection of transferred biomolecules, or filters to be placed on the anode side of a blotting sandwich can be soaked in a buffer that includes a compound as disclosed herein for semi-dry electroblotting. In both cases, the compound used in the anode buffer is not present in the cathode buffer, or is present in the cathode buffer in significantly reduced amount.

The methods and compositions can be applied to electroblotting systems that do not use separation of biomolecules on electrophoresis gels. For example, biological samples, cells, or lysates can be applied to membranes from unseparated fluid or suspended samples and fixed by electroblotting from unseparated fluid or suspended samples using the system described herein, in which an anodic chamber includes an anionic compound not present, or present in reduced amounts, in the cathodic chamber.

The invention provides methods of electroblotting and detecting biomolecules, in which the sensitivity of detection is improved by the use of particular compounds in the anode compartment that are not present, or present in significantly reduced amounts, in the cathode compartment. For example, the methods include blotting a separating gel comprising proteins using a dry electroblotting system of the present invention in which the anodic gel matrix includes an anionic buffer compound not present, or present in significantly reduced amount, in the cathodic gel matrix, and detecting one or more proteins on the blotting membrane using one or more of immunodetection, chromogenic detection, or chemiluminescent detection. The methods result in enhanced detection of proteins with respect to traditional blotting methods.

It is also possible, in accordance with additional embodiments of the present invention, to stain the molecular species during the electro-blotting procedure by including suitable staining materials or substances within the gels included in the electrode assemblies of the present invention, either by including the staining material or a source thereof in the electrically conducting electrodes used for applying the blotting currents or by including suitable stains within the gel bodies used for preparing the electrode assemblies. During the blotting procedures such stains or such in situ formed staining species may electrophoretically migrate towards the blotting membrane due to their electrical charge and stain the blotted molecular species on the blotting membranes. The staining may occur prior to the accumulation of the blotted species on the blotting membrane (while they are still in the resolving gel) or may occur on the blotting membrane. The advantage of using such in-situ staining methods is that a substantial amount of time and labor may be saved by eliminating a step of post-blotting staining.

The following descriptions are by way of illustration and not by way of limitation. Elements and features of the embodiments described can be combined with other embodiments of the invention to create new embodiments that are also included in the present invention.

Figure 2:
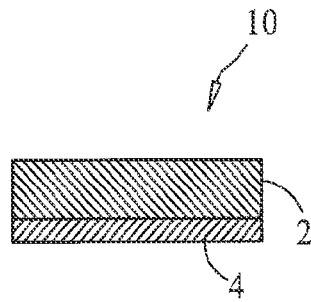
FIG. 2 is a cross sectional view of the electrode assembly illustrated in FIG. 1, taken along the lines II-II.

Reference is now made to FIGS. 1 and 2. FIG. 1 is a schematic isometric view of a disposable dry electroblotting electrode assembly, in accordance with an embodiment of the present invention and FIG. 2 is a cross sectional view of the electrode assembly illustrated in FIG. 1, taken along the lines II-II. The electrode assembly 10 includes an electrically conducting electrode 4 and a body of gel 2 attached to the electrode 4. The body of gel 2 may be any suitable gel, such as, but not limited to, a cross-linked polyacrylamide based gel, an agarose based gel, a gel including cross-linked polyacrylamide based gel and agarose or any other type of suitable gel or gel mixture known in the art.

The body of gel 2 includes a source of ions. The source of ions may be any suitable buffer solution incorporated in the body of gel 2 during the preparation of the body of gel 2, such as, but not limited to, any buffer known in the art to be used for blotting.

The electrically conducting electrode 4 may be any suitable electrically conducting electrode. Preferably, but not obligatorily, the electrode 4 is a thin metal foil or wire mesh, such as, but not limited to, a thin copper aluminum foil or mesh, or the like. One advantage of using copper electrodes in the electrode assemblies of the present invention is that when copper metal is included as the anode in an anodic electrode assembly of the present invention, almost no gas bubbles are released at the anode because copper ions are released from the copper anode into the body of gel and almost no electrolysis of water molecules occurs at the anode. Accordingly, in illustrative aspects, the electrode is made of a metal such as copper. However, other embodiments using electrodes including other metals may also be used, such as but not limited to silver, lead (Pb) or the like, which also reduce formation of gas bubbles near the anode.

The body of gel 4 may be cast onto the electrode 4 by suitably pouring a liquefied gel (such as, but not limited to, a warm liquefied agarose gel prepared in a suitable buffer solution) on the electrode 4 in a suitable casting chamber (not shown) and letting the gel solidify. Alternatively, a gel precursors mixture solution (such as, but not limited to, a suitable buffer solution containing a suitable acrylamide monomer with suitable bisacrylamide cross-linker and a suitable polymerization initiator, as is known in the art) may be poured onto the surface of the electrode 4 positioned in a suitable casting chamber and allowed to polymerize to form the body of gel 2.

It is also possible to attach a preformed body of gel 2 to the electrode 4 using other methods, or to form a gel attached to the electrode 4 by using suitable continuous gel extrusion methods.

It is noted that the Electrode 4 need not be made from a metal and may be made from or may include other suitable electrically conducting materials. For example, the electrode 4 may be made from a pliable sheet of graphite paper, or a sheet of other suitable pliable material (such as, for example a sheet made of a plastic material such as an organic polymer, or the like) coated with an electrically conducting material, such as but not limited to graphite powder or carbon particles, or the like. It is also possible to form the electrode 4 from an electrically conducting polymer, or from a suitable sheet of pliable material coated with an electrically conducting polymer, such as, but not limited to, polyaniline based electrically conducting polymers, polypyrrole based electrically conducting polymers, or any other suitable electrically conducting polymer known in the art.

Figure 3:
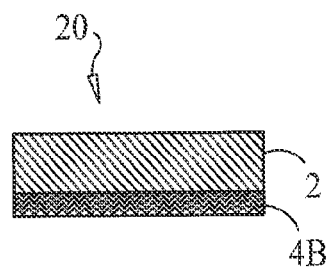
FIG. 3 is a schematic cross-sectional view illustrating a disposable dry electro-blotting electrode assembly having a mesh type or a woven type electrode.

Reference is now made to FIG. 3 which is a schematic cross-sectional view illustrating a disposable dry electroblotting electrode assembly having a mesh type or a woven type electrode. The electrode assembly 20 may include a body of gel 2 as described above and a mesh type or woven type electrically conducting electrode 4B. The electrode 4B may be preferably formed as a mesh or a grid composed of very thin electrically conducting metal wires such as, but not limited to, copper wires or aluminum wires or other types of metallic wires. Such metallic electrically conducting thin wires may be used to form a woven, electrically conducting, fabric-like electrode that may be advantageously more flexible and pliable than a foil made from the same metal. The thin metallic wires of the electrode 4B may also be formed into suitable braids (the braids are not shown in detail in FIG. 3) that may be woven into a fabric-like pliable electrically conducting electrode.

It is noted, however, the electrode 4B may also be formed from other types of thin electrically conducting non-metallic wires, such as, but not limited to, a pliable fabric made of carbon fibers or from fibers made from a non-electrically conducting material such as, for example, suitable polymer fibers or plastic fibers that are coated or plated or otherwise covered with a suitable electrically conducting material, such as, for example, carbon particles or graphite particles, or suitable metal particles or the like. Alternatively other types of electrically conducting fibers may also be used, such as, for example, fibers made of an electrically conducting organic polymer, or the like. The electrode 4B may thus be fabricated from composite thin fibers including suitable non-electrically conducting materials and suitable electrically conducting materials deposited or coated thereon or otherwise attached thereto.

It is noted that while typically the source of ions of the body of gel 2 may be any suitable buffer solution incorporated in the body of gel 2, alternatively or additionally, in accordance with an additional embodiment of the present invention, the body of gel 2 may include an ion exchange matrix capable of supplying ions for performing the electro-blotting.

Figure 4:
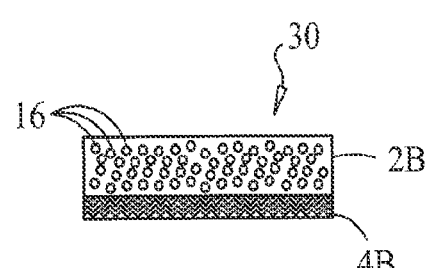
FIG. 4 is a schematic cross-sectional view illustrating a disposable dry electro-blotting electrode assembly having a mesh type electrode and a body of gel including an ion exchange matrix.

Reference is now made to FIG. 4 which is a schematic cross-sectional view illustrating a disposable dry electro-blotting electrode assembly having a mesh type electrode and a body of gel including an ion exchange matrix.

The electro-blotting electrode assembly 30 includes the electrode 4B as described in detail above and illustrated in FIG. 3. A body of gel 2B is juxtaposed with the electrode 4B by casting or polymerizing as described in detail above for the Electrode assembly 10 (of FIG. 1), or by any other suitable method. The body of gel 2B includes particles of a suitable ion exchange matrix 16 dispersed therein.

The ion exchange matrix 16 may be suitably dispersed in the gel material(s) used to prepare the body of gel 2B prior to polymerization and/or cross-linking of the gel. If an agarose-based gel is used, the ion exchange matrix may be added or dispersed in the gel when the gel is still in a liquefied state. If a polyacrylamide based gel is used for forming the body of gel 2B, the particles of ion exchange matrix 16 may be dispersed in the solution containing the gel precursors used for preparing the body of gel 2B.

Ion exchange matrix types useable in the electrode assemblies may include anion exchange matrices and cation exchange matrices, depending, inter alia, on the configuration used for electro-blotting. For example, if the electrode assembly 30 is used as a cathodic electrode assembly, the body of gel 2B may include an anion exchange matrix. If the electrode assembly 30 is used as an anodic electrode assembly, the body of gel 2B may include a cation exchange matrix.

It is noted that any of the above disclosed dry electro-blotting electrode assemblies 10, 20 and 30 (of FIGS. 1, 3 and 4, respectively) may be used as a cathodic electrode assembly for performing dry electro-blotting as is described in detail hereinafter. Additionally, any of the above disclosed dry electro-blotting electrode assemblies 10, 20 and 30 may also be used for forming an anodic dry electro-blotting electrode assembly by placing thereon or attaching thereto a suitable blotting membrane.

Figure 5:
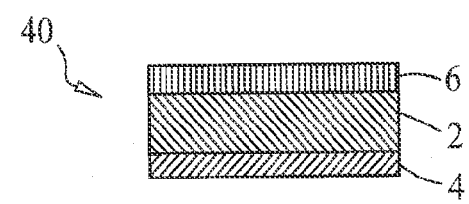
FIG. 5 is a schematic across-sectional view illustrating a disposable dry electro-blotting electrode assembly including a blotting membrane, in accordance with an embodiment of the present invention.

Reference is now made to FIG. 5 which is a schematic across-sectional view illustrating a disposable dry electro-blotting electrode assembly including a blotting membrane, in accordance with an embodiment of the present invention.

The electrode assembly 40 includes the electrode 4 and the body of gel 2 as disclosed in detail hereinabove. The electrode assembly 40 also includes a blotting membrane 6 juxtaposed with or disposed on the body of gel 2. The blotting membrane 6 may be any suitable blotting membrane, such as, but not limited to, a nitrocellulose blotting membrane, a PVDF based blotting membrane, an activated paper blotting membrane, an activated nylon blotting membrane, or any other suitable type of blotting membrane known in the art.

It is noted that while the electrode assembly 40 includes a single sheet of blotting membrane 6, it is possible, in accordance with another embodiment of the present invention to construct electrode assemblies containing multiple blotting membranes by simply attaching several stacked sheets of blotting membranes (not shown in FIG. 5) to the body of gel 2 of the electrode assembly. After performing the dry electro-blotting procedure as is disclosed hereinafter, the multiple blotting membranes of such a multi-membrane electrode assembly may be separated and used for various different purposes, such as, but not limited to, staining, immuno-detection, fluorescence visualization and the like, as is well known in the art.

Figure 6:
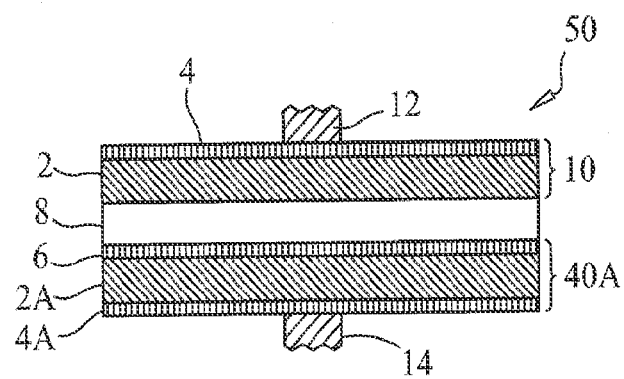
FIG. 6 is a schematic cross-sectional view illustrating a separating gel disposed between an anodic dry electro-blotting electrode assembly and a cathodic dry electro-blotting electrode assembly, in accordance with an embodiment of the dry electro-blotting method of present invention.

Reference is now made to FIG. 6 which is a schematic cross-sectional view illustrating a dry electroblotting system of the invention comprising a separating gel disposed between an anodic dry electroblotting electrode assembly and a cathodic dry electroblotting electrode assembly.

A blotting assembly 50 is shown disposed between two electrical contacts 12 and 14 of a blotting device (the blotting device itself is not shown in FIG. 6, for the sake of clarity of illustration). The blotting assembly 50 may include a gel 8 disposed between an anodic dry electro-blotting electrode assembly 40A and a cathodic dry electro-blotting electrode assembly 10 (see FIG. 2).

The anodic electrode assembly 40A may include an electrode 4A and a body of gel 2A. The electrode 4A may be similar to the electrode 4 described hereinabove (in FIGS. 1, 2 and 5) and the body of gel 2A may be similar to the body of gel 2 described hereinabove (in FIGS. 1, 2 and 5). However, the electrode 4A need not necessarily be identical to the electrode 4 of FIGS. 1, 2 and 5 in shape or composition. Similarly, while the body of gel 2A may be similar to the body of gel 2 of FIG. 5, this is not obligatory to practicing the invention. It is therefore noted that the body of gel 2A may have a similar or a different composition than the body of gel 2. The electrode assembly 40A also includes a blotting membrane 6 juxtaposed with or disposed on the body of gel 2A. The blotting membrane 6 may be any suitable blotting membrane, such as, but not limited to, a nitrocellulose blotting membrane, a PVDF based blotting membrane, an activated paper blotting membrane, an activated nylon blotting membrane, or any other suitable type of blotting membrane known in the art.

The cathodic dry electro-blotting electrode assembly 10 of the blotting assembly 50 may include the electrode 4 and the body of gel 2 as disclosed in detail hereinabove and illustrated in FIGS. 1, 2, and 5. The gel 8 is typically a separating gel that was used for electrophoretically separating or resolving different molecular species and therefore includes resolved molecular species therewithin. Gel 8 may be any type of gel useful for electrophoretic separation of biomolecules, and may include therein any separated molecular species known in the art.

For example, in accordance with one embodiment of the present invention, the gel 8 may be a standard polyacrylamide based gel that can optionally include sodium dodecyl sulfate (SDS) and various different separated proteins after performing an electrophoretic protein separation as is known in the art. In accordance with another embodiment of the present invention, the gel 8 may be an agarose based gel including separated nucleic acids (such as, for example, DNA or RNA or other types of polynucleotides or oligonucleotides). In accordance with other embodiments of the invention, the gel 8 may also be a two-dimensional (2D) separation gel on which the molecular species to be resolved were separated sequentially in directions orthogonal to each other, as is known in the art, or may be an isoelectric focusing gel as is known in the art.

The blotting assembly 50 may be formed by disposing the gel 8 between the anodic dry electro-blotting electrode assembly 40A and the cathodic dry electro-blotting electrode assembly 10 as shown in FIG. 6. For example, the anodic assembly 40A may be placed on a suitable flat surface and the gel 8 may be carefully manually laid on the surface of the blotting membrane 6. Care must be taken to avoid trapping of air bubbles between the gel 8 and the blotting membrane 6 during the placing of the gel 8 on the blotting membrane 6. The cathodic electrode assembly 10 may then be carefully placed on top of the gel 8 carefully avoiding the trapping of air bubbles between the upper surface of the gel 8 and the body of gel 2 of the electrode assembly 10.

The completed blotting assembly 50 may then be placed in contact with the electrical contacts 12 and 14 as shown in detail in FIG. 6, such that the contact 12 is in contact with the electrode 4 of the cathodic electrode assembly 10 and the contact 14 is in contact with the electrode 4A of the anodic electrode assembly 40A. A suitable voltage with the appropriate polarity is applied to the contacts 12 and 14 to perform the electro-blotting. The biomolecules are then electro-blotted onto the blotting membrane 6

After the dry blotting procedure is finished, the blotting assembly 50 may be disassembled and the blotting membrane 6 may be removed for further examination, staining (if necessary), visualization, and/or further use, as is known in the art.

It is noted that, in accordance with an additional embodiment of the present invention, the blotting assembly of FIG. 6 may include an additional blotting membrane (not shown in FIG. 6), such an additional blotting membrane (not shown) may be disposed between the body of gel 2 and the gel 8. This type of double-membrane blotting assembly may be useful in cases in which the molecular species that need to be blotted include both positively charged species and negatively charged species under the conditions present within the body of gel 8. For example, it is known in the art of protein separations that sometimes under specific pH conditions while most of the protein molecules are negatively charged, some protein molecules may have a net positive charge. Such positively charged protein molecules (or other positively charged non-protein molecular species) may electrophoretically migrate towards the cathode and will therefore not be blotted onto the blotting membrane 6 at the position illustrated in FIG. 6. When, in accordance with an additional embodiment of the present invention, an additional blotting membrane (not shown) is disposed between the body of gel 2 of the cathodic electrode assembly 10 and the body of gel 8, any such positively charged species may be blotted onto the additional membrane, and may therefore be detected and/or retrieved and/or used.

Thus, after the electro-blotting of such double-membrane containing electro-blotting assembly is completed, the assembly may be disassembled and both blotting membranes may be removed for further staining and/or detection and/or identification and/or visualization of the resolved species and/or isolation of such species for further use. It is also possible to stain such blotted species on one or on both of the two blotting membranes included in such double-membrane blotting assemblies by using any of the in-situ staining methods disclosed herein by including suitable staining species or substances either in the bodies of gel 2 and/or 2A of the electro-blotting assembly or by using silver metal included in the electrode of the anodic electrode assembly as disclosed in detail herein.

When a second blotting membrane is included in the electro-blotting assembly as disclosed hereinabove the additional blotting membrane may optionally be included as part of the cathodic electrode assembly. For example, a blotting membrane similar to or different than the blotting membrane 6 may be suitably juxtaposed with the surface of the body of gel 2 of the electrode assembly 10 of FIG. 2 opposite the side of the body of gel 2 to which the electrode 4 is attached, to form a blotting membrane including cathodic electrode assembly (not shown). Such blotting membrane including cathodic electrode assembly may be used together with the gel 8 and the anodic electrode assembly 40 (of FIG. 5) to form the double membrane electro-blotting assembly described hereinabove.

Alternatively, in accordance with another embodiment of the present invention it may be possible to use a separately provided blotting membrane (not shown) together with the electrode assembly 10 (of FIG. 2) and the electrode assembly 40 (of FIG. 5) and the gel 8, to form (manually, or with the help of a suitable de-bubbling device as disclosed in detail hereinafter) the double-membrane electro-blotting assembly described hereinabove.

It is noted that in forming of the blotting assembly 50 from the gel 8, the cathodic electrode assembly 10, and the anodic electrode assembly 40A, there is a tendency of air to become trapped between the gel 8 and the electrode assemblies 10 and 40A. Such trapped air bubbles may be undesirable since they may disturb the proper uniform flow of current through the blotting assembly 50.

The inventors of the present invention also provide here a novel device for reducing or eliminating the trapping of air bubbles in the blotting assembly during the forming thereof.

Figure 8:
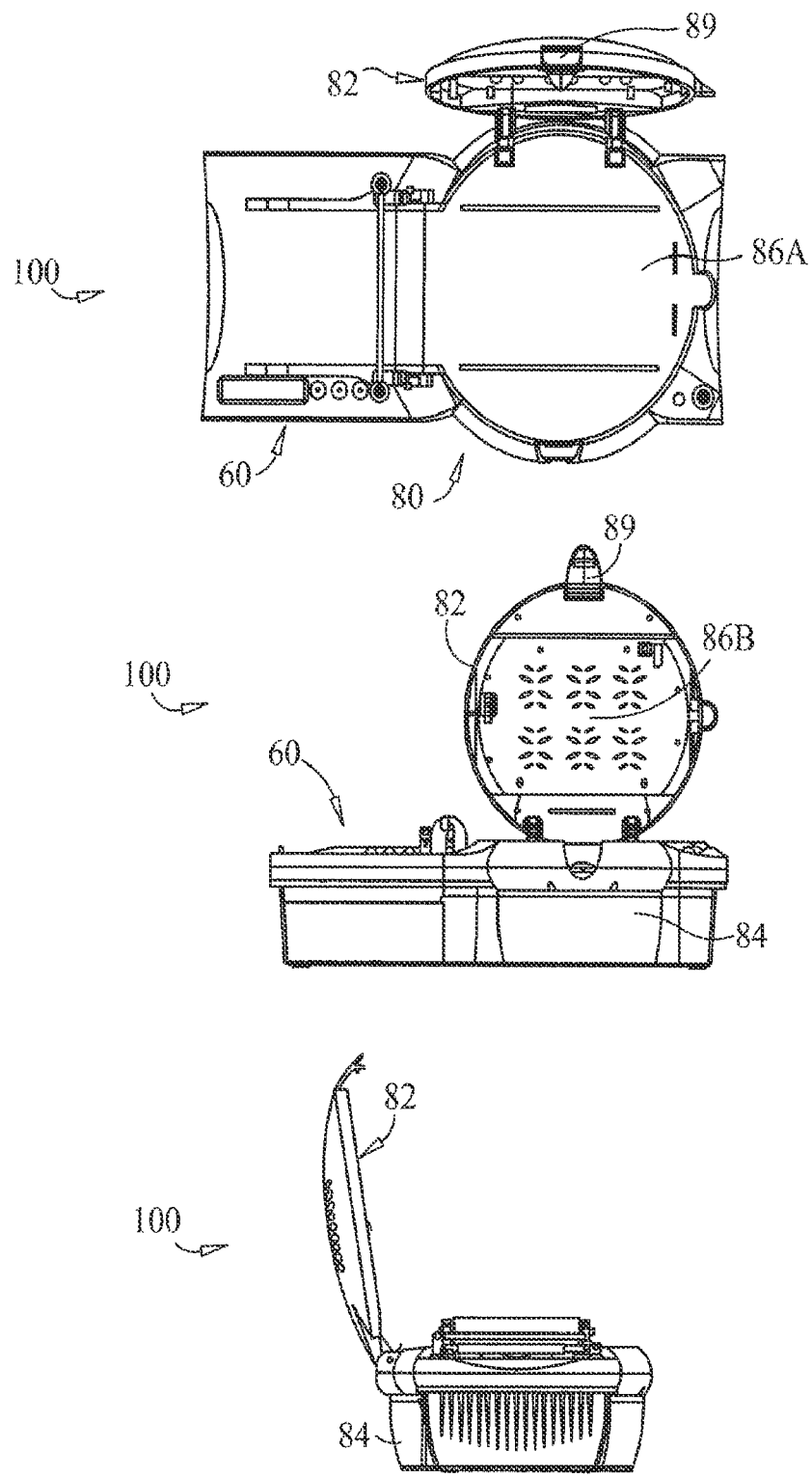
FIG. 8 provides several views of an apparatus of the present invention.
Figure 9:
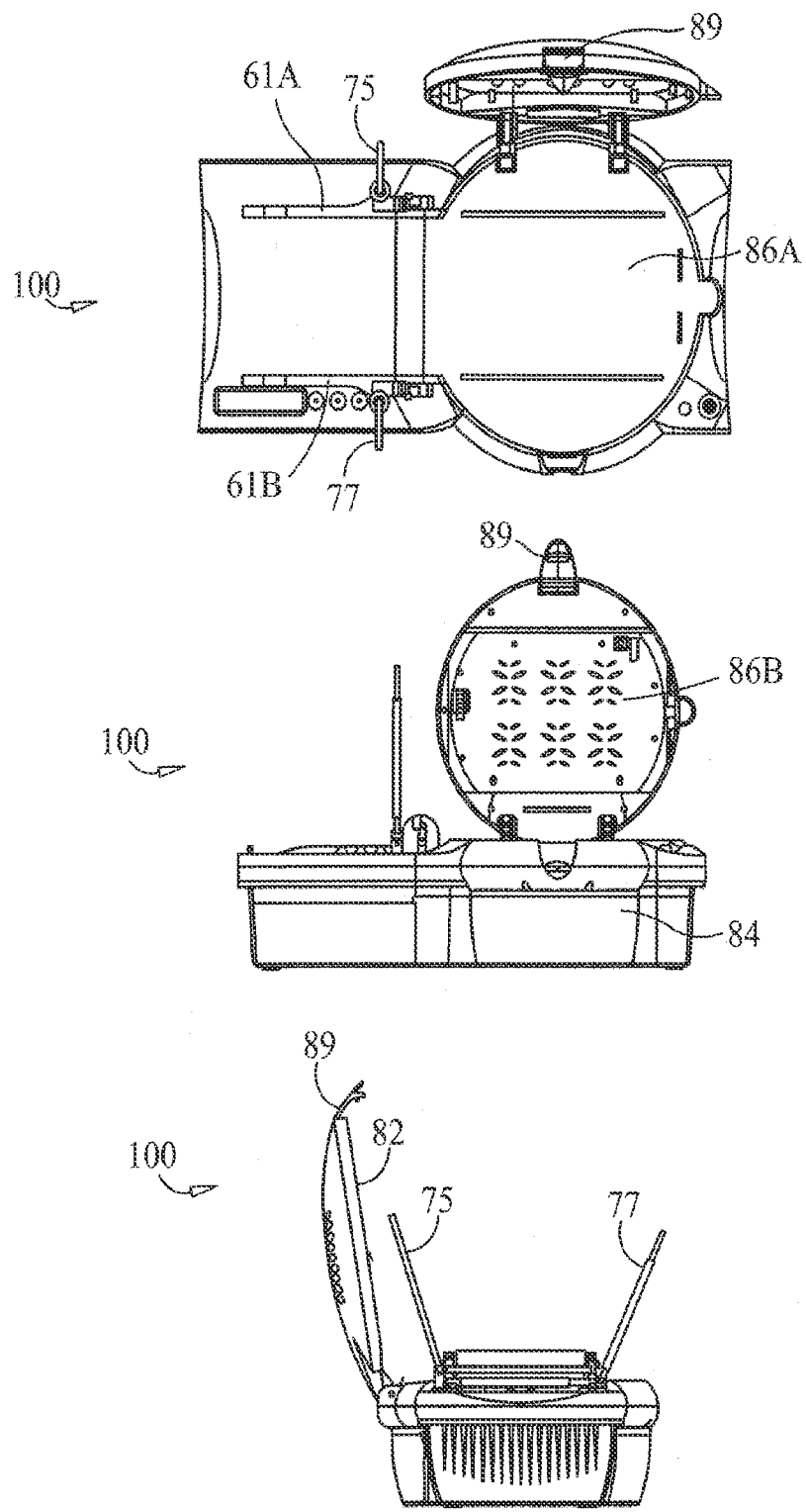
FIG. 9 provides several views of an apparatus of the present invention.
Figure 10:
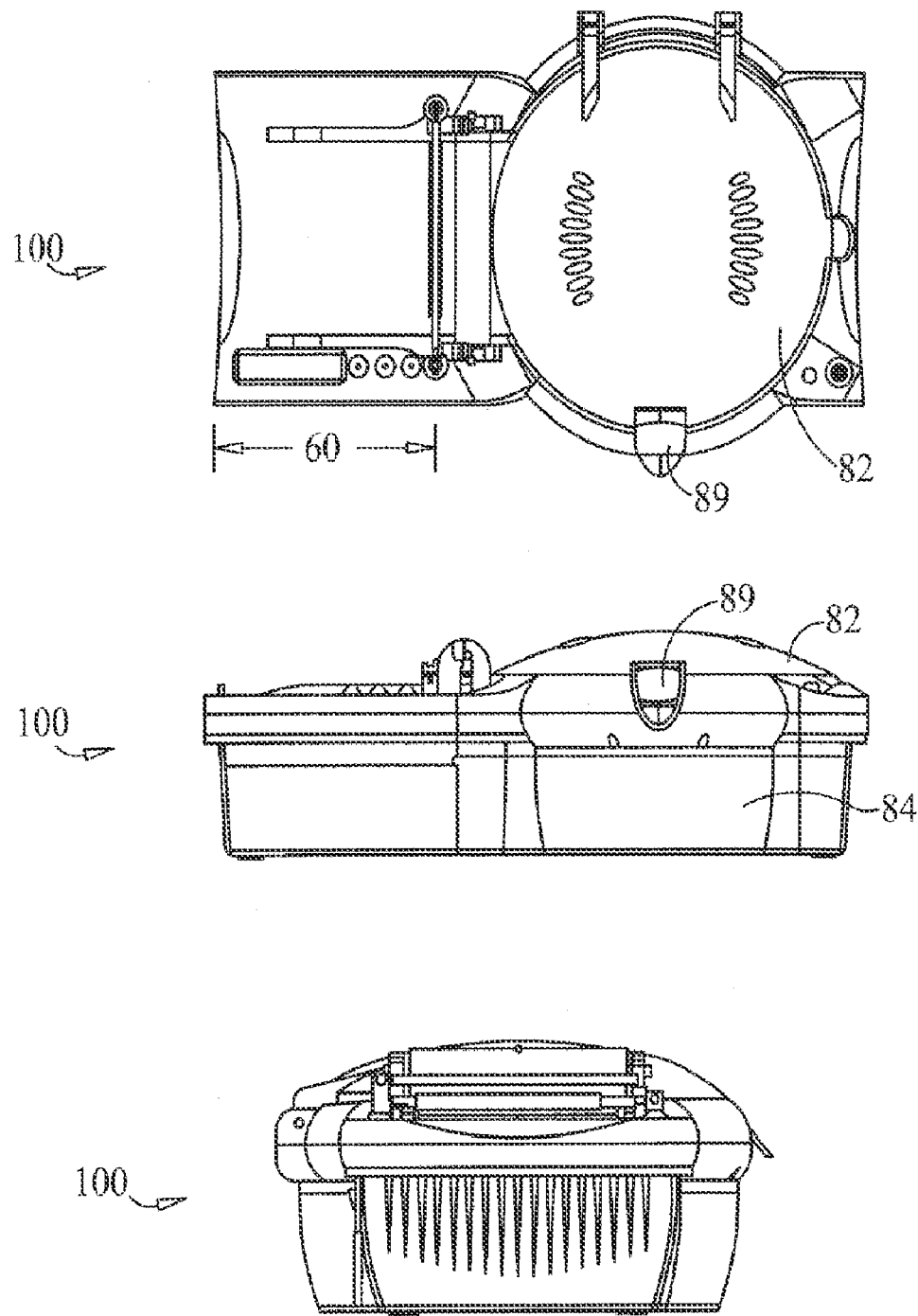
FIG. 10 provides several views of an apparatus of the present invention.

Reference is now made to FIGS. 7, 8, 9 and 10. FIG. 7 is a schematic cross-sectional view of part of a de-bubbling device usable in reducing the trapping of air bubbles while attaching the dry electro-blotting electrode assemblies of the present invention to a gel to be electro-blotted in accordance with an embodiment of the present invention. FIG. 8 is several views of an electro-blotting apparatus including a de-bubbling device combined with a dry electro-blotting unit, in accordance with yet another embodiment of the present invention. FIG. 9 also provides views of the electro-blotting apparatus of FIG. 8, illustrating the de-bubbling device with two separating elements in an open position and FIG. 10 provides several views of the electro-blotting apparatus of FIG. 8 and FIG. 9, illustrating the de-bubbling device of FIG. 9 with the lid closed and the two separating elements in a closed position.

In FIGS. 8 and 9, the electroblotting apparatus 100 includes a de-bubbling device 60 and an electroblotter device 80 combined in the same housing. The electro-blotter device 80 may include a flat surface 86A on which the blotting assembly 50 (or any other suitable blotting assembly) may be placed after it is formed, for performing electro-blotting thereon. The electro-blotter device 80 may also include a cover 82. The surface 86A includes an electrical contact (not shown). The electrical contact may or may not be spring loaded and may be used for applying a voltage to a blotting assembly (not shown) placed in contact with the surface 86A. Similarly, the surface 86B includes an electrical contact (not shown). The electrical contacts may or may not be spring loaded as is known in the art such that they may be pushed against the electrodes of the anodic and the cathodic electrode assemblies to ensure good electrical contact therebetween, and may be used for applying a voltage to a blotting assembly placed in contact with the surface 86B.

The apparatus 100 may also include a power supply (not shown in detail), which may be disposed within the housing 84 of the apparatus 100. Alternatively, the device 100 may have suitable sockets or contacts (not shown for the sake of clarity of illustration) for receiving external electrical power from a separated suitable power supply (not shown).

For performing electro-blotting, the blotting assembly 50 of FIG. 6 (or any other blotting assembly described herein) may be placed on the surface 86A and the cover 82 may be lowered until it touches the upper surface of the electrode 4 of the cathodic electrode assembly 10 of the blotting assembly 50 such that the electrical contact of the cover is in electrical contact with the electrode 4, and the electrical contact of the surface 86A is in electrical contact with the electrode 4A of the anodic electrode assembly 40A. The cover 82 may be held closed by a suitable latch 89 or by any other suitable locking mechanism, and a voltage difference may be applied between the electrical contacts to commence the electro-blotting. Details of the currents applied during electro-blotting and other details and parameters of the different electro-blotting procedures are given in Examples 1-14.

It is noted that while the apparatus 100 disclosed and illustrated herein includes a combination of a de-bubbling device 60 and an electro-blotter 80, this is not obligatory. In accordance with another embodiment of the invention the de-bubbling device may be implemented as a separate device for preparing blotting assemblies and the electro-blotting may be performed using any separate electro-blotter device as is known in the art.

Turning to FIG. 7, a de-bubbling device 60 includes a base 62 having a preferably flat surface 62A. A roller element 64 is attached to a movable supporting mechanism 70. The movable support mechanism 70 is attached to the base 62 through two holding arms 61A and 61B (best seen in FIG. 9), such that the roller 64 is held above the surface 62A of the base 62. The movable supporting mechanism 70 has a handle 74 that may be used for grasping and moving the movable supporting mechanism 70 in the directions labeled as 76A and 76B (FIG. 7). The roller element 64 is attached on an axle 65 which is rotatably and movably attached to the support mechanism 70. The support mechanism 70 and the axle 65 of the roller 64 are supported by two slotted support members 72 (only one of the support members 72 is seen in the cross-sectional view of FIG. 7), each having a vertical slot therein. The movable supporting mechanism 70 is configured to adjust the distance between the roller 64 and the surface 62A of the base 62, as disclosed in detail hereinafter.

The support mechanism 70 is configured such that it may be moved in the general directions indicated by the arrows labeled 76A and 76B. Moving the support mechanism 70 in the direction of the arrow 76B lifts up the roller element 64 as the axle 65 slides upwards within vertical slots of the support members 72 and increases the distance between the roller element 64 and the surface 62A of the base 62. Moving the support mechanism 70 in the direction of the arrow 76A lowers the roller element 64 down as the axle 65 slides downwards within the vertical slots and decreases the distance between the roller element 64 and the surface 62A of the base 62.

The de-bubbling device 60 also includes two movable separating members 75 and 77 movably attached to the base 62. The separating members 75 and 77 may be elongated rod-like members having a circular cross section, as shown in FIG. 9, but may also be implemented as elongated members having an elliptical cross-section or any other suitable cross-section. The separating members 75 and 77 may be moved so as to allow placement of a gel and/or a dry blotting electrode assembly (or assemblies) on the surface 62A of the base 62. For example, in FIG. 9, the separating members 75 and 77 are shown in an opened position and the support mechanism 70 is shown in an open position that maximizes the distance between the roller 65 and the surface 62A.

In FIG. 9, the separating members 75 and 77 of the de-bubbler are shown in an open position. In FIG. 10, the separating members 75 and 77 are shown in a closed position.

Returning to FIG. 7, the de-bubbling device 60 is shown in the process of forming a blotting assembly, in accordance with a method of the present invention. In accordance with one possible method of the present invention of forming a blotting assembly (such as, but not limited to, the blotting assembly 50 of FIG. 6), the movable support mechanism 70 may be opened to maximize the distance between the roller 65 and the surface 62A and the separating members 75 and 77 may be opened to the open position by moving them upward and to the sides (as seen in FIG. 9) to allow relatively free access to the surface 62A. An anodic dry-blotting assembly 40A (see FIG. 6), or any other type of suitable anodic electrode assembly described herein may be then placed on the flat surface 62A in the position shown in FIG. 7 with the electrically conducting electrode 4A in contact with the surface 62A and the blotting membrane 6 facing upwards.

The separating member 75 is then lowered until it touches the surface of the blotting membrane 6 of the anodic electrode assembly 40A. The gel 8 (which includes separated molecular species, as disclosed hereinabove with respect to FIG. 6) may then be placed on top of the surface of the blotting membrane 6 of the anodic electrode assembly 40A and over the separating member 75 as shown in detail in FIG. 7, such that part of the gel 8 is in contact with a part of the blotting membrane 6 while another part of the gel 8 is separated from the blotting membrane 6 by the separating member 75. The separating member 77 may then be lowered and placed in contact with the upper surface of the gel 8. The cathodic electrode assembly 10 (shown in detail in FIG. 2) may then be placed on top of the gel 8 and over the separating member 77 (as seen in FIG. 7), such that part of the body of gel 2 is in contact with a part of the gel 8 while another part of the body of gel 2 is separated from the gel 8 by the separating member 77. The electrically conducting electrode 4 of the cathodic electrode assembly 10 (shown in detail in FIG. 6) faces upwards (as seen in detail in FIG. 6).

The support mechanism 70 may then be lowered down (by moving the handle 74 in the direction represented by the arrow 76A of FIG. 7) until the lower part of the roller 64 touches the upper surface of the electrically conducting electrode 4 of the cathodic electrode assembly 10 and exerts a slight pressure thereon. The end of the entire combination including the gel 8 with the cathodic electrode assembly 10 and the anodic electrode assembly 40A may then be pulled in the direction represented by the arrow 85 of FIG. 7 to form the blotting assembly 50 (as shown in FIG. 6). As the combination including the gel 8, the cathodic electrode assembly 10 and the anodic electrode assembly 40A is pulled in the direction represented by the arrow 85, the separating members 75 and 77 maintain open spaces 91 and 92 between the gel 8 and the electrode assemblies 40A and 10, respectively, which facilitates the elimination or at least a significant reduction in the trapping of air bubbles between the gel 8 and the electrode assemblies 40A and 10.

Additionally, the pressure applied by the roller 64 advantageously ensures intimate contact between the blotting membrane 6 and the gel 8 and between the gel 8 and the body of gel 2 of the cathodic electrode assembly 10, which may improve the efficiency and uniformity of the electro-blotting.

Figure 17:
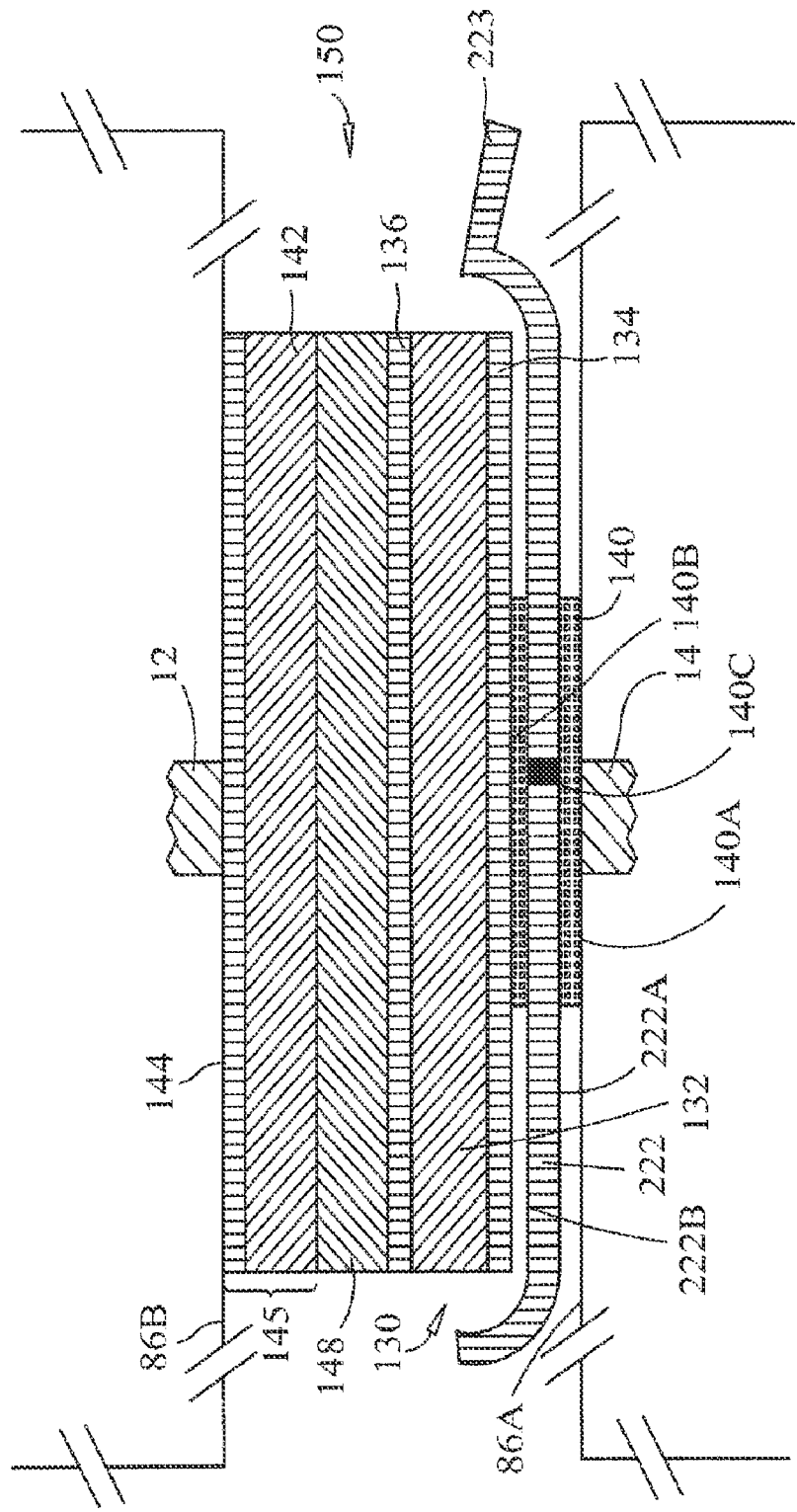
FIG. 17 is a cross-sectional view illustrating a blotting assembly including a suitable electrode built into a holding tray for performing dry electro-blotting while a blotting assembly is disposed within the holding tray.

Reference is now made to FIG. 17 which is a cross-sectional view of a blotting assembly including a suitable electrode built into the holding tray in order to enable performing of dry electro-blotting while a blotting assembly is disposed within the holding tray.

The blotting assembly 150 includes a holding tray 222. The holding tray 222 may include a pulling tab 223 similar in use to the pulling tab 223 of FIG. 17. The holding tray 222 includes an electrode assembly 140. The electrode assembly 140 may include two thin copper foil pieces 140A and 140B. The copper foil piece 140A is attached at the external surface 222A of the bottom part of the holding tray 222. The copper foil piece 140B is attached at the internal surface 222B of the bottom part of the holding tray 222. The copper foil pieces 140A and 140B are electrically coupled to each other by an electrically conducting connector 140C (such as, but not limited to, a short copper strip) passing through an opening in the holding tray 222.

It is noted that the copper foil pieces 140A and 140B may be substituted or replaced by suitable pieces of copper mesh or braided copper fabric or by any other suitable electrically conducting metal or material or combination of materials of any suitable shapes and/or configurations, including, but not limited to, all the types of electrically conducting materials disclosed herein.

The blotting assembly 150 also includes the anodic electrode assembly 130 as disclosed in detail herein. The electrode 134 of the anodic electrode assembly 130 is in electrical contact with the copper foil piece 140B, such that current may be passed to the electrode 134 through the electrode 140. The blotting assembly 150 also includes a gel 148 which includes separated molecular species (such as, but not limited to, proteins, DNA, RNA or the like) as described for the gel 8 of FIG. 6. The gel 148 is in contact with the blotting membrane 136 of the anodic electrode assembly 130.

The blotting assembly 150 also includes a cathodic electrode assembly 145 having a body of gel 142 and an electrode 144. The body of gel 142 and the electrode 144 of the anodic electrode assembly 145 may be similar to the body of gel 2 and the electrode 4 of the anodic electrode assembly 10 as disclosed in detail hereinabove. The body of gel 142 is in contact with the upper surface of the gel 148.

The entire blotting assembly 150 of FIG. 17 can be disposed between the surface 86A and the surface 86B of the electroblotter device 80 (see FIG. 8). An electrical contact on the surface 86B is in electrical contact with the electrode 144 of the cathodic electrode assembly 145 during operation of the device. The copper foil piece 140A is in electrical contact with an electrical contact of the housing 84 (see FIG. 8). The electrode 14 is disposed in a recess (not shown in detail for the sake of clarity of illustration) formed within the housing 84 and is exposed on the surface 86A of the housing 84. When the blotting assembly 150 is disposed in the position illustrated in FIG. 17, current may be applied to the blotting assembly 150 through the electrical contacts of the device and electroblotting may be performed as explained in detail herein.

It will be appreciated by those skilled in the art that the configuration of the electrode 140 of the holding tray 222 is not obligatory and may be varied in many ways, depending, inter alia, on the shape and position of the electrical contacts of the apparatus 100, the current intensities used, and other design considerations. Thus the positions and configuration of the electrical contacts of the device may be changed to adapt to different configurations of the holding tray 222 and the electrode 140.

For example, the opening at the bottom of the holding tray 222 may be omitted, and an elongated copper foil strip (not shown) may be attached on the internal surface 222B of the holding tray 222. One end of the copper strip may make electrical contact with the electrode 134 while the other end of the copper strip (not shown) may terminate on the upper surface of the pulling tab 223. In such an arrangement, the electrode 14 (or another different suitable electrode) may be electrically connected to the end of the copper foil strip positioned on the pulling tab 223 to apply current to the electrode 134. Such a configuration may be easier and less expensive to manufacture than the configuration with the electrode 140 shown in FIG. 17.

Many such variations permutations and combinations of the position, shape, size and material composition of the various types of electrodes shown in the drawing figures and disclosed herein may be possible for the person skilled in the art. The configurations disclosed this application and illustrated in the drawings are therefore given by way of example only and are not intended to limiting the possible scope of the present invention.

Examples 1-14 below include detailed non-limiting practical applications of the methods and electrode assemblies of the present invention.

EXAMPLE 1

An E-PAGE 6% 96 gel (commercially available as Catalogue Number EP096-06 from Invitrogen Corporation, Carlsbad, Calif.) was run using an E-Base electrophoresis apparatus (commercially available as Catalogue Number EBM-03 from Invitrogen Corporation) for 14 min (program EP). Five microliters of E-PAGE See Blue pre-stained protein standard (commercially available as Catalogue Number LC5700 from Invitrogen Corporation, USA) were loaded in each of the wells of the E-PAGE gel cassette. After the completion of the run, the cassette was opened to remove the gel.

The gel with the resolved protein standards separated thereon was sandwiched between an anodic electrode assembly and a cathodic electrode assembly as disclosed in detail with respect to FIG. 6 hereinabove. The anodic electrode assembly included a copper mesh electrode made of a piece of braided copper mesh having a length of twelve centimeters and a width of eight centimeters cut from a Kiel copper pbn11 fabric, (commercially available from Shildex, Germany). The braided copper mesh electrode was juxtaposed with one surface of a gel slab of the same surface area (8×12 centimeters) having a thickness of three millimeters. The gel slab was made of a polyacrylamide/agarose composite (10% polyacrylamide with 5% cross-linking and 0.5% agarose) including 120 mM Bis Tris, 95 mM Tricine, 95 mM BES, 0:3% SDS and 20% ethylene glycol. A nitrocellulose membrane having a pore size of 0.2 microns (commercially available as Catalogue Number BA83 from Schleicher & Schuell Bioscience Inc., GMBH) with dimensions of 8×12 centimeters was juxtaposed with the second surface of the gel slab on the side of the gel slab opposite the side to which the copper mesh electrode was attached.

The cathodic dry blotting electrode assembly was made from a second slab of gel having dimensions of 8×12 centimeters and a thickness of one and a half millimeters (1.5 millimeters) and having the same composition as the gel slab used in making the anodic electrode assembly as described in detail hereinabove.

The blotting assembly was formed by placing the anodic electrode assembly on top of the surface 62A of the de-bubbling device 60 described hereinabove and illustrated in FIGS. 7-10 and then placing the EPAGE 96 gel with the resolved protein standards included therein on the surface of the blotting membrane of the anodic dry-blotting electrode assembly and then placing the cathodic blotting electrode assembly on the EPAGE 96 gel. The details of forming the blotting assembly were as described in detail hereinabove with respect to FIGS. 6-10.

The resulting blotting assembly sandwich including the EPAGE 96 gel, the cathodic electrode assembly and the anodic electrode assembly was pulled through the roller 64 of the de-bubbling device 60 to eliminate air bubbles between the layers. Then a pressure was applied on the blotting assembly sandwich and a voltage difference of 35V was applied to the electrodes for seven minutes. At the end of this dry electro-blotting process, the blotting membrane and the EPAGE 96 gel were separated from the sandwich and the pre-stained markers were visually observed on the blotting membrane while none of the pre-stained markers were seen on the EPAGE 96 gel indicating efficient transfer of the protein standards from the gel to the blotting membrane. After completion of protein dry electroblotting performed using the dry electroblotting electrode assemblies of the present invention, the nitrocellulose blotting membrane showed that efficient transfer of pre-stained proteins had occurred.

The use of copper metal in the anodic electrode assemblies of the present invention substantially reduces or eliminates the release of gas and formation of bubbles between the electrically conducting copper electrode and the attached body of gel and therefore enables the use of larger currents leading advantageously to a faster blotting time. The typical (initial) current densities used for electro-blotting were about thirty milliamperes per square centimeter (30 mA/cm$^2$). In contrast, most commercially available semi-dry blotters are typically limited to current densities in the range of 2-6 milliamperes per square centimeter (2-6 mA/cm$^2$). This advantageously allows the shortening of the time required for blotting, and therefore saves time and allows the performance of more blotting procedures per each blotting apparatus in a given time period.

EXAMPLE 2

The electroblotting was performed as described in Example 1 above except that the electrically conducting electrode of the anodic electrode assembly was made from aluminum foil (Cat No. 1170, commercially available from 3M, USA) instead of the braided copper mesh used in the anodic electrode assembly of Example 1. The electro-blotting using such aluminum electrode resulted in somewhat less efficient blotting than the results of Example 1.

EXAMPLE 3

The electro-blotting was performed as described in Example 1 above except that the composition of the body of gel used in the anodic electrode assembly was as follows: a volume of gel comprising 4% agarose, 120 mM Bis Tris, 95 mM Tricine, 95 mM BES, 0.3% SDS and 20% ethylene glycol was mixed with same volume of wet fibrous cellulose phosphate based cation exchange matrix (Catalogue Number p11 commercially available from Whatman International Ltd., UK) loaded with Bis Tris ions, and the composition of the gel used to prepare the cathodic electrode assembly was as follows: a volume of gel comprising 4% agarose, 120 mM BIS TRIS, 95 mM Tricine, 95 mM BES, 0.3% SDS and 20% ethylene glycol was mixed with same volume of pre-swollen micro-granular diethylaminoethyl (DEAE) cellulose based anion exchange matrix (Catalogue Number DE52, commercially available from Whatman International Ltd., UK) loaded with Tricine ions. The blotting was carried out as detailed hereinabove for Example 1. Good blotting results were obtained.

Additional experiments were also performed in which only the gel body of the cathodic electrode assembly included an ion exchange matrix. The anodic electrode assembly and the EPAGE 96 gel were prepared as disclosed in detail in Example 1 hereinabove. The composition of the gel used to prepare the cathodic electrode assembly was as follows: a volume of gel comprising 4% agarose, 120 mM Bis Tris, 95 mM Tricine, 95 mM BES, 0.3% SDS and 20% ethylene glycol was mixed with same volume of pre-swollen micro-granular diethylaminoethyl (DEAE) cellulose based anion exchange matrix (Catalogue Number DE52, commercially available from Whatman International Ltd., UK) loaded with Tricine ions. The blotting was carried out as detailed hereinabove for Example 1. Good blotting results were also obtained.

EXAMPLE 4

An E-PAGE™ 48 8% gel (commercially available as Catalogue Number EP048-08 from Invitrogen Corporation, USA) was run for 23 minutes in an E-Base electrophoresis apparatus (commercially available as Catalogue Number EB-M03 from Invitrogen Corporation, USA) using program EP. Five microliters (5 µl) samples of a Benchmark protein ladder solution (commercially available as Catalogue Number 10747-012 from Invitrogen Corporation, USA) were loaded into several wells of the E-PAGE™ 48 gel. After the electrophoretic run, the gel was taken out of the cassette and electroblotted for five minutes as described in detail in Example 1. The anodic electrode assembly used for blotting was similar to the anodic electrode assembly used in Example 1 above, except that the electrically conducting electrode of the anodic electrode assembly used in Example 4 differed from the electrically conducting electrode used in Example 1. The electrically conducting electrode of the anodic electrode assembly used in Example 4 was prepared as follows: a copper mesh electrode was made of a piece of braided copper mesh having a length of twelve centimeters and a width of eight centimeters cut from a Kiel copper pbn11 fabric, (commercially available from Shildex, Germany). The braided copper mesh electrode was coated with a silver emulsion (elcolit 370, commercially available from Elosol Ltd., Zurich, Switzerland). The body of gel juxtaposed with this electrode had the same dimensions and the same composition as the body of gel used in the cathodic electrode assembly of Example 1. The blotting membrane and the cathodic electrode assembly used in Example 4 were as described in detail in Example 1.

During the blotting step, silver ions formed at the anode from the silver metal atoms coated on the copper mesh migrated toward the blotting membrane and interacted with the proteins that simultaneously migrated from the E-PAGE 48 gel to the blotting membrane. After the blotting was completed, the blotting membrane was separated from the blotting assembly and exposed to UV light for two minutes and then exposed to ambient light (in the room) for ten additional minutes. Silver stained protein bands could be seen on the blotting membrane.

Thus, using a silver-containing electrode enables the simultaneous blotting and staining of resolved molecular species such as proteins, polypeptides, polynucleotides and oligonucleotides (including, but not limited to, DNA, RNA and the like) and any other type of silver stainable molecular species known in the art.

EXAMPLE 5

An E-PAGE 48 8% gel (commercially available as Catalogue Number EP048-08 from Invitrogen Corporation, USA) was run for 23 minutes using an E-Base electrophoresis apparatus (commercially available as Catalogue Number EB-M03 from Invitrogen Corporation, USA), using program EP. Five microliter (5 µl) samples of a Benchmark protein ladder solution (commercially available as Catalogue Number 10747-012 from Invitrogen Corporation, USA) were loaded into several wells of the E-PAGE 48 gel. After the run the gel was taken out of the cassette and electro-blotted for five minutes as described in detail in Example 1. The anodic electrode assembly was as described in detail in Example 1 hereinabove. The cathodic electrode assembly was prepared as follows: the body of gel matrix for the cathodic electrode assembly was prepared by separately (without the copper mesh electrode) forming a gel slab having the dimensions of eight centimeters by twelve centimeters and a thickness of 1.5 millimeters. The composition of this gel slab was as described hereinabove for the cathodic gel matrix used in the cathodic electrode assembly of Example 1.

The slab of cathodic gel matrix was then soaked overnight in fifty milliliters of a solution of coomassie blue R-250 (0.03% coomassie blue R-250 in 10% acetic acid and 30% methanol aqueous solution). The cathodic gel matrix slab was then carefully wiped dry and manually juxtaposed with a piece of braided copper mesh having a length of twelve centimeters and a width of eight centimeters cut from a Kiel copper pbn11 fabric, (commercially available from Shildex, Germany), to form a cathodic electrode assembly. A blotting assembly was prepared from the E-PAGE 48 gel, the anodic electrode assembly and the cathodic electrode assembly by using the de-bubbler device 60 as described in detail in Example 1. The blotting assembly was then electro-blotted for five minutes using a voltage difference of 25 Volts. During the electroblotting run, the negatively charged Coomassie ions migrated electrophoretically towards the blotting membrane just behind the proteins and stained the protein bands on the blotting membrane. At the end of the five minute electroblotting period, the blotting assembly was disassembled and the blotting membrane was removed for observation. Stained protein bands could be visually observed on the blotting membrane.

EXAMPLE 6

An E-PAGE 48 8% gel (commercially available as Catalogue Number EP048-08 from Invitrogen Corporation, USA) was run for 23 minutes using an E-Base electrophoresis apparatus (commercially available as Catalogue Number EB-M03 from Invitrogen Corporation, USA), using program EP. Five microliter (5 µl) samples of a Benchmark protein ladder solution (commercially available as Catalogue Number 10747-012 from Invitrogen Corporation, USA) were loaded into several wells of the E-PAGE 48 gel. After the run the gel was taken out of the cassette and electro-blotted as described in detail in Example 1. The electro-blotting duration was five minutes at 25 volts. The anodic electrode assembly was the same as the anodic electrode assembly used in Example 1. The cathodic electrode assembly was prepared as follows: the body of gel for the cathodic electrode assembly was prepared by separately (without the copper mesh electrode) forming a gel slab having the dimensions of eight centimeters by twelve centimeters and a thickness of 1.5 millimeters. The composition of this gel slab was as described hereinabove for the cathodic gel used in the cathodic electrode assembly of Example 1.

The slab of gel matrix was then soaked overnight in fifty milliliters of a ready made solution of Sypro Ruby blot stain (commercially available as Catalogue Number S11791 from Molecular Probes, OR, USA). The gel matrix slab was then carefully wiped dry and manually juxtaposed with a piece of braided copper mesh having a length of twelve centimeters and a width of eight centimeters cut from a Kiel copper pbn11 fabric, (commercially available from Shildex, Germany), to form a cathodic electrode assembly. A blotting assembly was prepared from the E-PAGE 48 gel, the anodic electrode assembly and the cathodic electrode assembly by using the de-bubbler device 60 as described in detail in Example 1. The blotting assembly was then electroblotted for five minutes using a voltage difference of 25 Volts. During the electroblotting run, the negatively charged Sypro Ruby ions migrated electrophoretically towards the blotting membrane just behind the proteins and stained the protein bands on the blotting membrane. At the end of the five minute electroblotting period, the blotting assembly was disassembled and the blotting membrane was removed. The blotting membrane was visualized using a UV light source (Alfaimager, commercially available from Alfa Innotech, Calif., USA) and fluorescent stained protein bands were observed on the blotting membrane.

EXAMPLE 7

An E-Gel 48 2% gel (commercially available as Catalogue Number G8008-02 from Invitrogen Corporation, USA) comprising ethidium bromide was run for 20 minutes using program EG on an E-Base electrophoresis apparatus (commercially available as Catalogue Number EB-M03 from Invitrogen Corporation, USA). One microliter (1 µl) samples (applied in a total aliquot volume of 15 µl) of low mass ladder (commercially available as Catalogue Number 10068-013 from Invitrogen Corporation, USA) were loaded into each of several wells of the E-Gel. After the completion of the electrophoretic separation run, the gel was visualized using a UV trans-illuminator and the ethidium stained bands could be seen. Then, the E-gel was removed out of the E-gel cassette and electro-blotted as described in detail in Example 1. The cathodic electrode assembly and the anodic electrode assembly were prepared as described in Example 1. A blotting assembly was prepared from the E-gel 48 2% gel, the anodic electrode assembly and the cathodic electrode assembly by using the de-bubbler device 60 as described in detail in Example 1. The electro-blotting duration was five minutes at 25 volts.

After the electro-blotting was completed, the E-gel 48 (2%) gel was visualized using a model TFX-20M UV transilluminator (commercially available from Vilber Lourmat, France) and no fluorescent bands were found on it, indicating efficient transfer of the DNA bands to the blotting membrane. The blotting membrane was then also visualized over a Model DR-45M dark reader (commercially available as from Clare Chemical Research Inc., CO, USA) and photographed. All the blotted bands were readily visualized.

EXAMPLE 8

The iBlot™ electroblotting apparatus is an electronic power supply unit controlled by electronic circuitry, capable of generating defined electric fields according to specified programs. The dry electroblotting apparatus is designed for use with dry electro-blotting electrode assemblies which act as ion reservoirs. In this system, the ions required for driving the samples from the separation gel are incorporated in gel matrices (including, in the case of the anode assembly, an ion exchange matrix), instead of liquid buffers or soaked papers, rendering the process clean and easy, requiring minimal manual work. Transfer speed is increased through the creation of high field strength and high currents, using the short distance between the electrodes and the built-in power supply.

The device is assembled of a Cycloloy plastic shell with stainless steel and aluminum components of a "de-bubbler" for mechanical elimination of bubbles between the transfer membrane, separation gel and the electrode assemblies (electrodes plus juxtaposed gel matrices). The apparatus includes an integral power supply (100-240V, AC; 50-60 Hz) capable of producing 225 W at currents of ~6 A at 25V that produces the driving force for the ions and samples. The power supply is controlled by three electronic circuits. A software driven control panel enables the user to choose between programs for the best transfer results from their separation system. Three running programs have been developed and programmed into the iBlot™ for optimal transfers. The first, running at 25 Volts, can transfer samples from one midi sized or two mini sized 1 mm thick NuPAGE gels and E-PAGE gel at 7 and 8 minutes respectively and a 23 V program can be used for the transfer of one mini NuPAGE gel in 7 minutes. A third program that runs at 20V is included for applications where a longer transfer is required. Four printed circuit boards (PCBs) carry the electronic components required to carry the systems logic unit, modify voltage and currents for display and logic, and powering the electro-blotting process. In addition, the unit has a USB port, used for uploading new programs and downloading transfer data.

The device is turned on by a power switch located near the power inlet and the USB port at the back of the device. A six digit liquid crystal display (LCD) indicates the program number and blotting time. Three buttons located near the LCD control program or time selection. The red Start/Stop button activates the run, then stops, and resets the program in subsequent press. A red and green LED indicates running status or errors. Aural alerts are available to indicate run start, run end, and malfunctions.

The transfer area includes an anode positioning area that provides an electrical contact on which the stack (anode assembly, separating gel, cathode assembly) are positioned for transfer, and a lid that is positioned over the stack during transfer. The lid has an area for securing a sponge and also includes an electrical contact. The electrical contacts of the anode positioning area and lid are gold coated copper-beryllium.

Disposable electrode assemblies are provided in plastic trays that are lamination-sealed to protect the assemblies from dehydration, light, and gasses. The electrode assemblies come in two sizes: mini for transferring one mini gel and regular size, for transferring two mini gels or one midi or E-PAGE gel.

The composition of the gel matrix of the anodic assembly is provided in Table 1.

TABLE 1

Composition of the anodic gel matrix

| Material | Final concentration or volume |
| --- | --- |
| Distilled Water | 52.8% |
| Ethylene Glycol (EG) | 20% |

TABLE 1-continued

Composition of the anodic gel matrix

| Material | Final concentration or volume |
| --- | --- |
| 1H Benzotriazole (BTA) | 0.001M |
| Bis Tris | 240 mM |
| Tricine | 190 mM |
| BES | 95 mM |
| Agarose D-5 | 0.50% |
| Propyl Paraben (PP) | 0.02% |
| Methyl Paraben (MP) | 0.18% |
| Acryl/BIS 19:1 Solution | 10% |
| TEMED | 0.067% |
| Ammonium Persulfate (APS) | 0.017% |

The composition of the gel matrix of the cathodic gel matrix, prior to mixing with DEAE-Cellulose/Tricine, is provided in Table 2. DEAE-Cellulose/Tricine is mixed 1:1 with the below composition to make the cathodic gel body.

TABLE 2

Composition of the Cathodic gel matrix (prior to mixing with ion exchange matrix)

| Material | Final concentration or volume |
| --- | --- |
| Bis-Tris | 120 mM |
| Tricine | 95 mM |
| Agarose D-5 | 3% |
| Ethylene glycol | 20% |
| BTA | 1 mM |
| Methyl Paraben (MP) | 0.18% |
| Propyl 4-hydroxybenzoate | 0.02% |

Materials:
The iBlot™ unit
Anode Assembly (Bottom Stack)
Cathode Assembly (Top Stack)
Disposable sponge
The user's separation gel with separated samples iBlot™ Setup:
The iBlot™ is connected to the AC outlet using the cable supplied with the kit. When the separation gel run is almost completed, the iBlot™ is turned ON by pressing the power switch on the back of the apparatus. The fan in the unit begins to run and the digital display is activated. Text appears in the display, and after a few seconds of stabilization, the default parameters (program, time) of operation are displayed. The default parameters can be changed by pressing the cyclic selection button which toggles between the selection of run programs, run minutes and run seconds. The currently selected item blink. By using the up and down buttons (+/−), the values may be changed to the desired parameters (seconds are incremented or decreased in 10-sec steps).

Each time the iBlot™ is turned on, the preset default parameters appear: The software version and the program and run time from the previous run.

Table 3 specifies the recommended programs and their running parameters for different separation gels.

TABLE 3

Recommended Run Parameters

| Gel Type | Program | Time |
| --- | --- | --- |
| All Mini Gel, 1 | P2 (23 V) | 6-7 min. |
| 2 mini gels on one regular stack | P1 (25 V) | 6-8 min. |

TABLE 3-continued

Recommended Run Parameters

| Gel Type | Program | Time |
| --- | --- | --- |
| All Midi Gel, 1 mm | P1 (25 V) | 7-8 min. |
| E-PAGE 48, 8% | P1 (25 V) | 8 min |

Based on the initial results, blotting conditions (time or program) can be modified to get optimal results.

To assemble the iBlot™ for Blotting using the de-bubbler (e.g., for E-PAGE), open the lid, the metal spacers of the debubbler are pulled up and the de-bubbler roller is removed. The spacers (bars), de-bubbling roller, and blotting surfaces must be clean and smooth. If not, the parts can be wiped with a damp cloth. Open the package labeled: "Transfer Stack BOTTOM" that includes an anodic assembly that includes a blotting membrane and is provided in a plastic tray. Place it left of the de-bubbling roller, so that the pull tab of the tray is on the right side of the de-bubbler. Slide it all the way to the left, until it is blocked by the stoppers on the left side of the surface. Next, wet spacer #1 (with the white sleeve) and place it on the membrane. Next, the separation gel is placed over spacer #1, aligned to the right corner of the BOTTOM Stack or anode assembly (the wells of the gel should face up). No special treatments are needed before placing the separation gel on the debubbler. Wet Spacer #2 and place it over the gel.

Open the TOP stack (cathode assembly), discard the red plastic tray, and place it on top of spacer #2 with the copper electrode side facing upwards. All layers need to be aligned to the right in order to perform efficient de-bubbling. Insert the de-bubbler roller into the two axe grooves and press it to the right, under the dent. The pull tab is held while the roller is lowered to its lowest location.

Pull both stacks and separation gel together using both pull tabs through the de-bubbler towards the blotting area, in one smooth movement, until it reaches the barriers on the blotting surface. The layers should be aligned to the right.

Place the disposable sponge on the inner side of the lid, so that the white-side is facing towards the user, and the metal contact is to the top right. There are small protrusions on the lid that hold the sponge in its place. The sponge will absorb excessive amounts of fluid that might be generated during the blotting and exert even pressure on the surface of the stacks. Close the lid and secure the latch. The red light should be on, indicating a closed circuit. The transfer starts when the Start/Stop button is pressed. The red control light will then turn green. At the end of the blotting procedure, the digital display blinks and a "beep" sound is repeated. The lid of the iBlot™ may then be opened, and the sponge and TOP stack (cathode assembly) are discarded.

The membrane is carefully peeled from the gel and the regular procedure of detection can be carried on. Do not let the membrane dry!

The used BOTTOM stack (anode assembly) is discarded along with its plastic tray. The sponge, filter paper, TOP and BOTTOM stacks (electrode assemblies) are not be reused. If necessary, the blotting surface can be cleaned with a damp cloth. At this point, the iBlot™ is ready for another run (no cooling period is required). Otherwise, the power of the iBlot™ should be turned off.

Assembling the iBlot™ for blotting separation gels 1.5 mm thick or less:

Open the lid and raise both metal spacers. The blotting surfaces need to be clean. If not, wipe all parts with a damp cloth. Place the BOTTOM Stack directly on the blotting surface (under the round lid), aligned to the right-hand stoppers. No bubbles should be noticed between the membrane, and the BOTTOM (anodic) gel beneath it. Place the separation gel on the membrane of the BOTTOM (anodic) stack. On top of it, place a filter paper wet with water (filter papers are included in the kit). Use the hand-held roller supplied with the kit to purge trapped air bubbles between the membrane and separation gel.

Open a TOP stack (cathode assembly), discard the plastic tray and put the stack on top of the filter paper. Place a sponge on the inner side of the lid so that the white side is facing towards you and the metal contact is to your right. There are small protrusions that hold the sponge in its place. The sponge will absorb fluid that might be generated during the blotting and exert even pressure on the surface of the stacks. Close the lid and secure the latch. The red light should be on, indicating a closed circuit. The transfer starts when the Start/Stop button is pressed. The red control light will then turn green. At the end of the blotting procedure, the digital display blinks and a "beep" sound is repeated. The lid of the iBlot™ is opened, and the sponge and TOP stack (cathode assembly) are discarded. The membrane is carefully peeled from the gel and the regular procedure of detection can be carried on.

The used BOTTOM stack (anode assembly) is discarded along with its plastic tray. The sponge, filter paper, TOP and Bottom stacks (electrode assemblies) can not be reused. If necessary, the blotting surface can be cleaned with a damp cloth. At this point, the iBlot™ is ready for another run (no cooling period is required). Otherwise, the power of the iBlot™ should be turned off.

TABLE 4 the basic operation conditions of the iBlot ™

| Components of iBlot ™ system | |
| --- | --- |
| BOTTOM gel stack (anode assembly) | Chemical composition specified in Table 1 |
| Transfer membrane | Nitrocellulose, Pore size 0.22 µ, BA-83 S&S |
| TOP Stack (cathode assembly) | Chemical composition specified in Table 2 |
| Duration of transfer | 7 min for NuPAGE, 8 min for E-PAGE 48, 8% |
| Voltage | P1 (25 V) |
| Separation gel | (Examples) NuPAGE bis-tris 4%-12%, 1 mm, NP0322BOX, or E-PAGE 48, 8%, EP048-08 |

EXAMPLE 9

An E-PAGE™ 8% 48 gel (EP048-08, Invitrogen, Carlsbad, Calif.) was run using an E-Base™ (Invitrogen EBM-03) integrated power supply for 25 min (program EP). 5 ul of See-Blue® Plus2 prestained protein standard (LC5700, Invitrogen, Carlsbad, Calif.) were loaded in all wells.

After the run, the cassette was opened to extract the gel.

An anode assembly was built by placing using a 3 mm thick gel made of polyacrylamide/agarose composite (10% total acrylamide with 5% crosslinkage and 0.5% agarose) comprising 240 mM Bis Tris, 190 mM Tricine, 95 mM BES, and 20% ethylene glycol on top of a 85×140 mm copper electrode (Kiel copper pbn11 fabric, Shildex, Germany). The anode assembly (gel matrix plus electrode) was in a plastic tray which was placed on the base of the iBlot™ dry electroblotting apparatus. A nitrocellulose membrane 0.2 u (BA83 S&S, Germany) with the same dimensions as the electrode and gel matrix was placed on top of the anodic gel matrix. The electrophoresed gel was placed on top of the membrane.

The cathodic gel matrix (composition: 50% of DE-52 ion exchange matrix loaded with Tricine ions and then mixed 1:1 with a gel solution that was made of: 3% agarose, 120 mM Bis-Tris and 95 mM Tricine) of gel thickness 19 mm had an electrode of the same type as the anode attached to the top of it. The cathode assembly (gel matrix plus electrode) was placed on top of the separation gel with the exposed electrode facing up.

Figure 11:
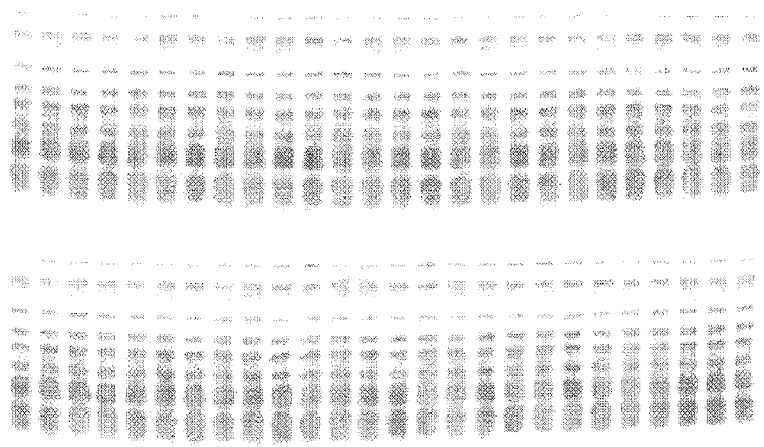
FIG. 11 is a photograph of a blotting membrane after completion of dry electroblotting transfer from a protein separating gel, performed using the dry electro-blotting electrode assemblies of the present invention, in accordance with an embodiment of the present invention.

The lid of the dry electroblotter apparatus was closed, applying pressure to the stack and a 25V voltage was applied for 8 minutes. At the end of this process the stack was disassembled and the membrane was removed. The prestained markers can be clearly seen on the membrane (FIG. 11).

EXAMPLE 10

A NuPAGE® 4-12% gel (Invitrogen) was run using MES buffer according to the manufacturer's instructions. Five (5) microliters of SeeBlue® Plus2 pre-stained markers were run in lanes 1, 2, 3, 11, and 12. One (1) microliter of Magic Mark™ XP western blot markers were loaded in lanes 4, 5, and 8. 0.5 microliters of Magic Mark™ XP markers were loaded in lanes 6, 7, 9, and 10.

After the run, the cassette was opened to extract the gel.

An anode assembly was positioned on the iBlot™ electroblotter base. The anode assembly included a 85×140 mm copper electrode (Kiel copper pbn11 fabric, Shildex, Germany) juxtaposed with a 3 mm thick gel of the same area comprising 2% agarose, 240 mM Bis Tris, 190 mM Tricine, 95 mM BES, 20% alumina, 0.5% chitosan, and 10% ethylene glycol. The anode assembly was in a plastic tray. A nitrocellulose membrane 0.2 u (BA83 S&S, Germany) with the same dimensions as the anodic gel matrix and electrode was placed on top of the anodic gel matrix. The electrophoresed gel was placed on top of the membrane. A cathode assembly having a cathodic gel matrix (composition: 50% of DE-52 ion exchange matrix loaded with Tricine ions mixed with 50% gel composed of: 3% agarose, 120 mM Bis-Tris and 95 mM Tricine, gel thickness of 19 mm) juxtaposed with same electrode type (but with no blotting membrane) was placed on top of the separation gel with the exposed electrode facing up.

Figure 12:
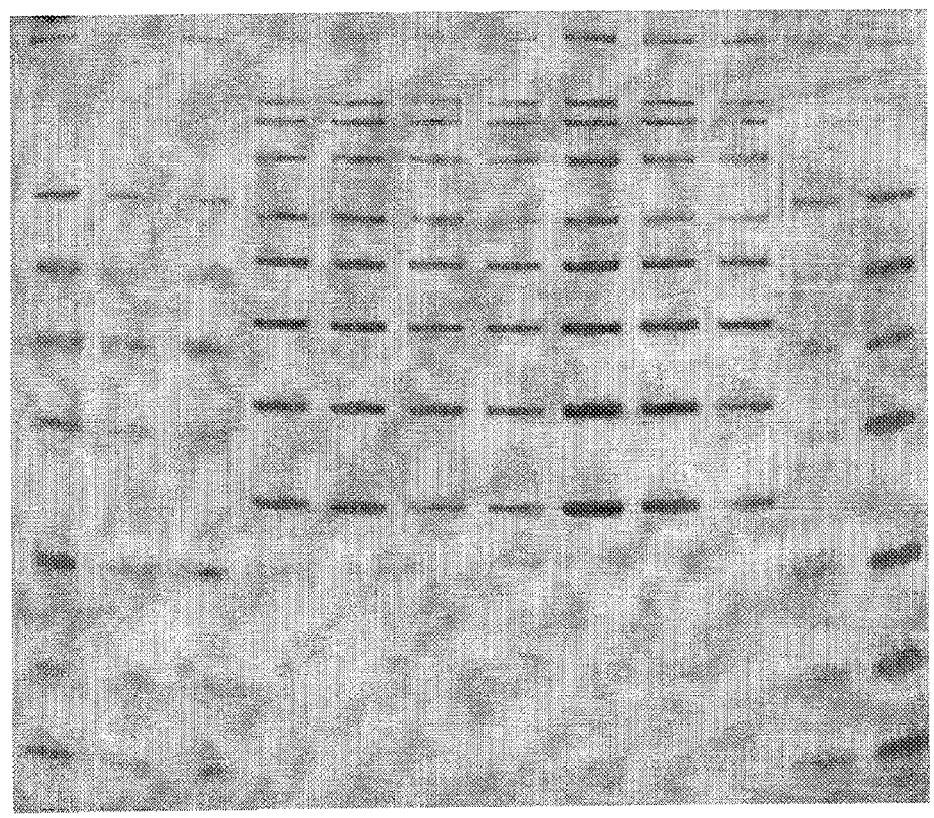
FIG. 12 is a photograph of a blotting membrane after completion of protein dry electroblotting transfer from a resolving gel, performed using the dry electro-blotting electrode assemblies of the present invention.

The lid of the dry electroblotting apparatus was then closed, applying pressure to the stack and a 20V voltage was applied for 6.5 minutes. At the end of this process the Westernbreeze® Chromogenic detection kit (Invitrogen, Carlsbad, Calif.) was used to detect the MagicMark™ protein standards (lanes 4-10), which can be detected using this kit without antibody incubation. The results are shown in FIG. 12.

EXAMPLE 11

An E-PAGE™ 8% 48 (Invitrogen EP048-08) gel was run using an E-Base™ integrated power supply (Invitrogen EBM-03) for 25 min (program EP). The samples were loaded according to Table 5, in which BSA refers to bovine serum albumin, SB+2 refers to SecBlue® Plus2 prestained protein standard, MMXP refers to Magic Mark™ XP western blot markers, and BM refers to BenchMark™ protein ladder, all from Invitrogen (Carlsbad, Calif.).

TABLE 5

| Lane | Sample | Amount |
|---|---|---|
| 1 | SB + 2 | 5 ul |
| 2 | BSA | 500 ng |
| 3 | BSA | 250 ng |
| 4 | BSA | 100 ng |
| 5 | BSA | 50 ng |
| 6 | BSA | 25 ng |
| 7 | BSA | 10 ng |
| 8 | BSA | 5 ng |
| 9 | SB + 2 | 5 ul |
| 10 | BM | 5 ul |
| 11 | BM | 2.5 ul |
| 12 | | |
| 13 | SB + 2 | 5 ul |
| 14 | MMXP | 10 ul |
| 15 | MMXP | 10 ul |
| 16 | MMXP | 5 ul |
| 17 | MMXP | 5 ul |
| 18 | MMXP | 2.5 ul |
| 19 | MMXP | 2.5 ul |
| 20 | MMXP | 1 ul |
| 21 | MMXP | 1 ul |
| 22 | MMXP | 0.5 ul |
| 23 | MMXP | 0.5 ul |
| 24 | SB + 2 | 5 ul |
| 25 | SB + 2 | 5 ul |
| 26 | BSA | 500 ng |
| 27 | BSA | 250 ng |
| 28 | BSA | 100 ng |
| 29 | BSA | 50 ng |
| 30 | BSA | 25 ng |
| 31 | BSA | 10 ng |
| 32 | BSA | 5 ng |
| 33 | SB + 2 | 5 ul |
| 34 | BM | 5 ul |
| 35 | BM | 2.5 ul |
| 36 | | |
| 37 | SB + 2 | 5 ul |
| 38 | MMXP | 10 ul |
| 39 | MMXP | 10 ul |
| 40 | MMXP | 5 ul |
| 41 | MMXP | 5 ul |
| 42 | MMXP | 2.5 ul |
| 43 | MMXP | 2.5 ul |
| 44 | MMXP | 1 ul |
| 45 | MMXP | 1 ul |
| 46 | MMXP | 0.5 ul |
| 47 | MMXP | 0.5 ul |
| 48 | SB + 2 | 5 ul |

After the run, the cassette was opened to extract the gel.

An anode assembly was built by placing a 3 mm thick gel matrix made of polyacrylamide/agarose composite (10% total acrylamide with 5% crosslinkage and 0.5% agarose)) comprising 60 mM Bis Tris, 95 mM Tricine, 95 mM BES, 20% ethylene glycol, and 6% acetic acid on top of a 85×140 mm copper electrode (Kiel copper pbn11 fabric, Shildex, Germany). The electrode assembly was in a plastic tray which was positioned on the base of the iBlot™ dry electroblotting apparatus. A nitrocellulose membrane 0.2 u (BA83 S&S, Germany) with the same dimensions was placed on top of the anodic gel matrix. The electrophoresed gel was placed on top of the membrane. The cathode gel was 50% of DE-52 ion exchange matrix loaded with Tricine ions mixed with 50% gel solution that was made of: 3% agarose, 120 mM Bis-Tris, 95 mM Tricine, and 0.5% Direct blue 71 stain (Sigma), having a thickness of 19 mm. An electrode of the same type as the anode was placed top of the cathode gel. The cathode assembly (gel matrix plus electrode) was placed on top of the separation gel with the exposed electrode facing up.

Figure 13:
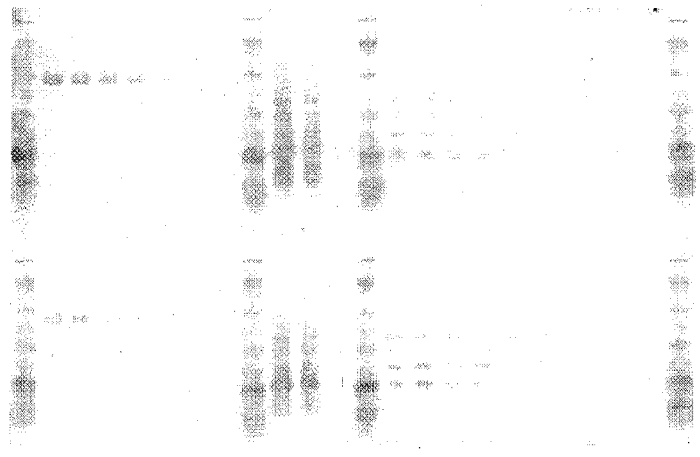
FIG. 13 is a photograph of a blotting membrane after completion of protein dry electroblotting transfer from a separating gel, performed by the dry electroblotting method of the present invention.

The lid of the dry electroblot apparatus was closed, applying pressure to the stack and a 25V voltage was applied for 8 minutes. During this process the BSA bands and the markers were stained. At the end of the transfer the stack was disassembled and the membrane was removed. The stained bands can be clearly seen on the membrane to a sensitivity of 10 nanograms (FIG. 13).

EXAMPLE 12

An E-PAGE™ 8% 48 gel (EP048-08, Invitrogen, Carlsbad, Calif.) was run using an E-Base™ (Invitrogen EBM-03) integrated power supply for 25 min (program EP)). The samples were loaded exactly as in Example 11 (according to Table 5), in which BSA refers to bovine serum albumin, SB+2 refers to SeeBlue® Plus2 prestained protein standard, MMXP refers to Magic Mark™ XP western blot markers, and BM refers to BenchMark™ protein ladder, all from Invitrogen (Carlsbad, Calif.).

After the run, the cassette was opened to extract the gel.

An anode assembly was built by placing a 3 mm thick gel made of polyacrylamide/agarose composite (10% total acrylamide with 5% crosslinkage and 0.5% agarose) comprising 60 mM Bis Tris, 95 mM Tricine, 95 mM BES, 20% ethylene glycol, and 6% acetic acid on top of a 85×140 mm copper electrode (Kiel copper pbn11 fabric, Shildex, Germany). The gel/electrode assembly was in a plastic tray which was placed on the base of the iBlot™ dry electroblotting apparatus. A nitrocellulose membrane 0.2 u (BA83 S&S, Germany) with the same dimensions was placed on top of the anodic gel matrix. The electrophoresed gel was placed on top of the membrane. The 19 mm thick cathode gel (composition: 50% of DE-52 ion exchange matrix loaded with Tricine ions mixed with 50% gel solution that was made of: 3% agarose, 120 mM Bis-Tris, 95 mM Tricine, and 1% copper phthalocyanine tetra sulfonate stain (Sigma)) had an electrode of the same type as the anode attached to the top of it. The cathode assembly (gel plus electrode) was placed on top of the separation gel with the exposed electrode facing up.

Figure 14:
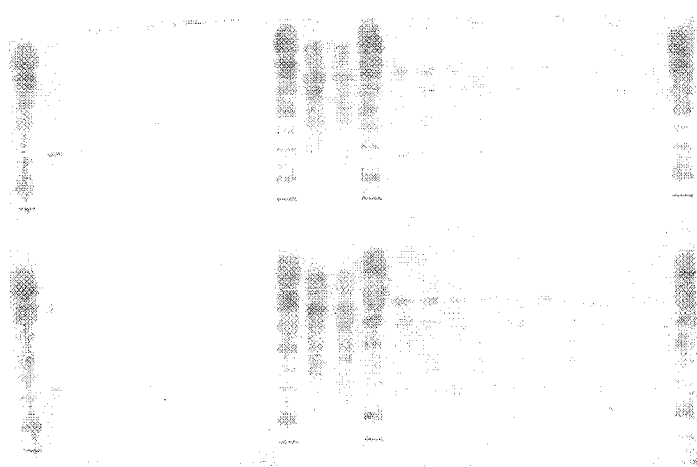
FIG. 14 is a photograph of blotting membrane after completion of protein dry electro-blotting transfer from a separating gel, performed by the dry electro-blotting method of the present invention.

The lid of the dry electroblot apparatus was closed, applying pressure to the stack and a 25V voltage was applied for 8 minutes. During this process the BSA bands and the markers were stained. At the end of the transfer the stack was disassembled and the membrane was removed. The stained bands can be clearly seen on the membrane to a sensitivity of 25 nanograms (FIG. 14).

EXAMPLE 13

Two identical Novex® MIDI gels (Invitrogen) were run according to manufacture's instructions with the SeeBlue protein standards, M, and a human colorectal adenocarcinoma cell lysate (SW480). Samples were loaded according to Table 6.

TABLE 6

| Lane | Sample | Volume |
|------|--------|--------|
| 1 | SB | 5 ul |
| 2 | SW480 | 2 ul |
| 3 | SW480 | 1 ul |
| 4 | SW480 | 0.5 ul |
| 5 | SW480 | 0.25 ul |
| 6 | SB | 5 ul |
| 7 | MMXP | 2 ul |
| 8 | MMXP | 1 ul |
| 9 | MMXP | 0.5 ul |
| 10 | SB | 5 ul |

Figure 15A:
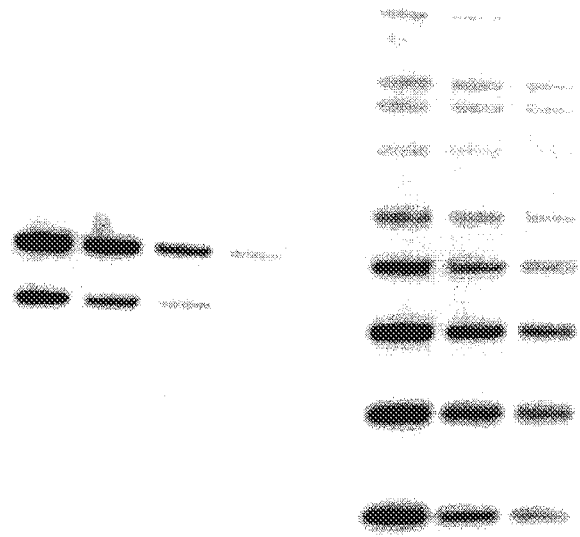
FIG. 15 is a photograph of a blotting membrane after completion of protein dry electro-blotting transfer from a separating gel performed by the dry electro-blotting method using of the present invention and immunodetection using chemiluminescent reagents.
Figure 15B:
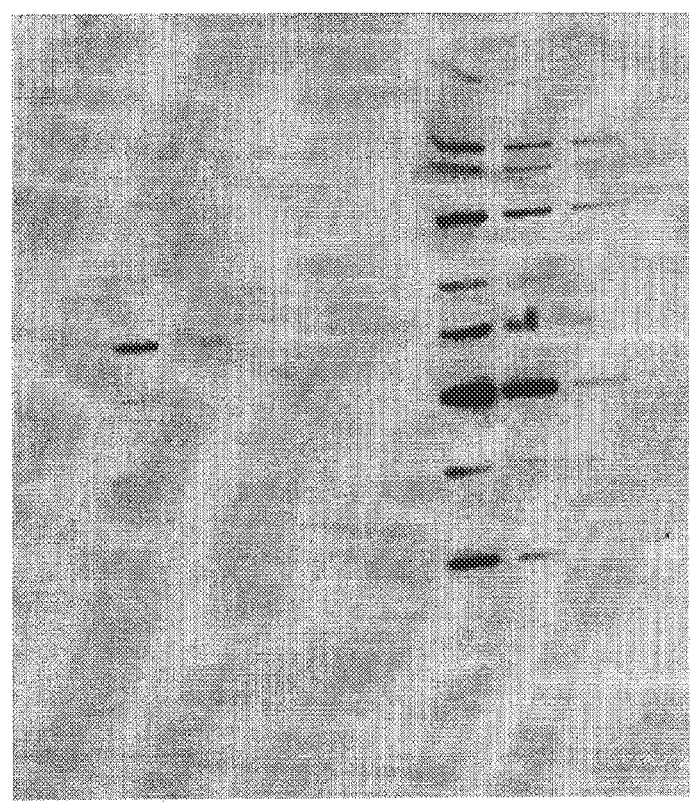

One gel was transferred using the iBlot using the protocol of Example 8, and the other gel was semi-dry electroblotted. Anti-tubulin (1:10,000) and anti-actin (1:5000) were used to detect proteins on the membranes and chemiluminescent detection was performed using the WesternBreeze chemiluminescent detection kit (Invitrogen). FIG. 15A shows the iBlot electroblotting gives more intense signal than does the conventional semi-dry transfer blot (FIG. 15B). The iBlot electroblotted membrane allows detection of four fold less protein, detecting tubulin and actin protein in 0.25 micoliters of lysate (lane of FIG. 15A) than conventional semi-dry transfer, in which the detection limit is 1.0 micoliters of lysate (lane 3 of FIG. 15B).

EXAMPLE 14

Two identical Tris-Acetate 3-8% gels (Invitrogen) were run according to manufacture's instructions with the samples given in Table 7:

TABLE 7

| Lane | Sample | Volume |
|------|--------|--------|
| 1 | SB + 2 | 5 ul |
| 2 | SW480 | 0.25 ul |
| 3 | SW480 | 0.5 ul |
| 4 | SW480 | 1 ul |
| 5 | SW480 | 2 ul |
| 6 | SW480 | 25 ng |
| 7 | SB + 2 | 5 ul |
| 8 | MMXP | 0.5 ul |
| 9 | MMXP | 1 ul |
| 10 | MMXP | 2 ul |
| 11 | MMXP | 4 ul |
| 12 | SB + 2 | 5 ul |

Figure 16:
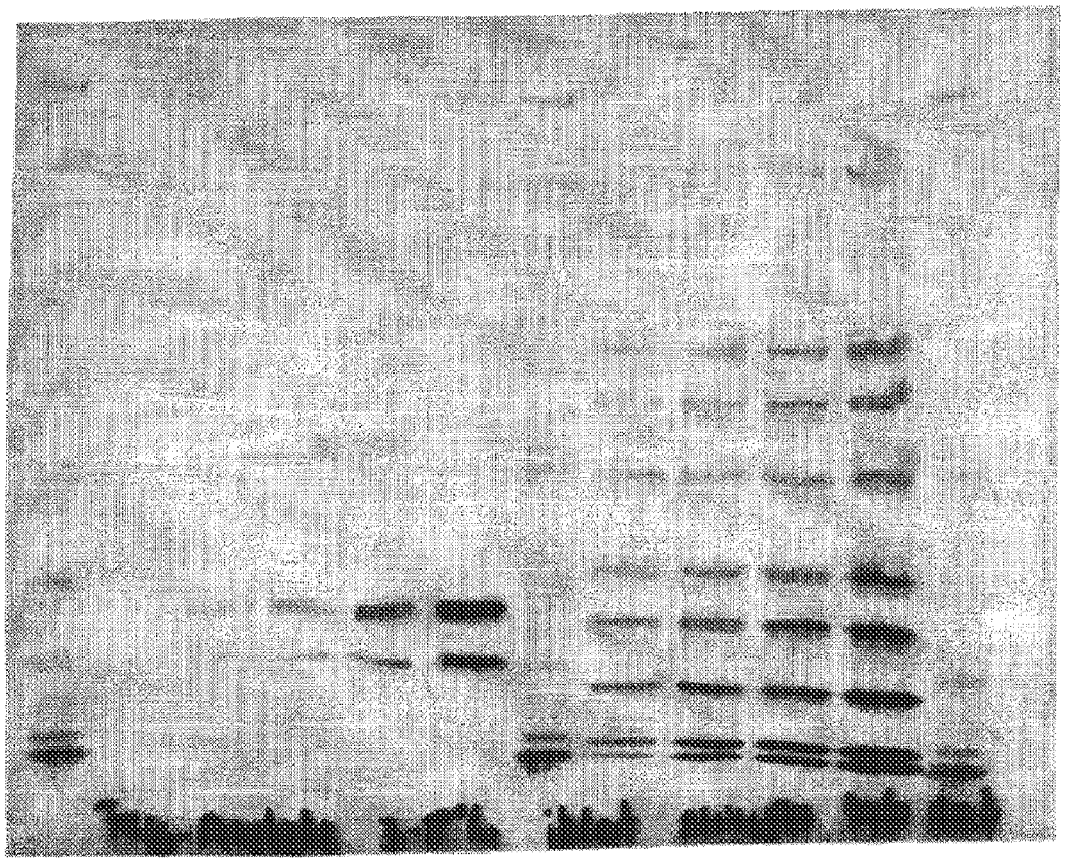
FIG. 16 is a photograph of a blotting membrane after completion of protein dry electro-blotting transfer from a separating gel performed by the dry electro-blotting method using of the present invention and immunodetection using chromogenic reagents.

One gel was transferred using the iBlot using the protocol of Example 8, and the other gel was semi-dry electroblotted. Anti-tubulin (1:10,000) and anti-actin (1:5000) were used to detect protein on the membranes and chromogenic detection was performed using the WesternBreeze chromogenic detection kit (Invitrogen). The iBlot gives more intense signal than does the conventional semi-dry transfer blot. Tubulin and actin proteins can be detected from 0.5 microliters of lysate electroblotted using the iBlot (FIG. 16, lane 3), whereas 4 microliters of the same lysate are required to obtain a similar level of detection on a wet-blotted membrane.

Variations in the different materials used to implement the electrode assemblies and the various devices disclosed herein are possible and may easily be implemented by a skilled artisan without undue experimentation. The invention illustratively described herein suitably may be practiced in the absence of any element(s) not specifically disclosed herein. Thus, the terms and expressions which have been employed are used as terms of description and not of limitation, equivalents of the features shown and described, or portions thereof, are not excluded, and it is recognized that various modifications are possible within the scope of the invention.

Although the invention has been described in substantial detail with reference to specific embodiments, those of ordinary skill in the art will recognize that changes may be made to the embodiments specifically disclosed in this application and these modifications and improvements are within the scope and spirit of the invention. The examples provided herein are representative of specific embodiments, are exemplary, and are not intended as limitations on the scope of the invention. Embodiments of the invention are set forth in the following claims.

Headings are for the convenience of the reader and are not intended to limit the invention in any way.

The entirety of each patent, patent application, publication and document referenced herein hereby is incorporated by reference, including all tables, drawings, and figures. All patents and publications are herein incorporated by reference to the same extent as if each was specifically and individually indicated to be incorporated by reference. Citation of the above patents, patent applications, publications and documents is not an admission that any of the foregoing is pertinent prior art, nor does it constitute any admission as to the contents or date of these publications or documents.

What is claimed is:

1. A method for electroblotting a sample from an electrophoresis gel to a blotting membrane comprising:
providing at least a first and a second pre-packaged ion reservoir, said first ion reservoir comprising a blotting membrane juxtaposed with a matrix having a source of ions sufficient for performing electroblotting, and said second ion reservoir comprising a matrix having a source of ions for performing electrophoresis;
forming an electrophoresis transfer stack by juxtaposing an analysis gel with the blotting membrane juxtaposed with the first ion reservoir, and electrically coupling the first ion reservoir to a first electrode and juxtaposing said second ion source with the analysis gel and electrically coupling said second ion source to a second electrode, wherein said analysis gel comprises one or more biomolecules to be transferred to the blotting membrane; and
passing a current of at least about 10 mA/cm$^2$ between the first electrode and the second electrode such that at least a portion of the one or more biomolecules are transferred from the analysis gel to the blotting membrane.

2. The method according to claim 1, wherein the current passed between the first electrode and the second electrode is at least about 15 mA/cm$^2$.

3. The method according to claim 1, wherein the current passed between the first electrode and the second electrode is at least about 25 mA/cm$^2$.

4. The method according to claim 1, wherein the current passed between the first electrode and the second electrode is at least about 30 mA/cm$^2$ or more.

5. The method according to claim 1, wherein the current passed between the first electrode and the second electrode is at least between about 10 mA/cm$^2$ to about 50 mA/cm$^2$.

6. The method according to claim 1, wherein the current passed between the first electrode and the second electrode is at least between about 20 mA/cm$^2$ to about 40 mA/cm$^2$.

7. The method according to claim 1, wherein the current passed between the first electrode and the second electrode is at least between about 25 mA/cm$^2$ to about 35 mA/cm$^2$.

8. The method according to claim 1, wherein the current passed between the first electrode and the second electrode is at least about 30 mA/cm$^2$.

9. The method according to claim 1, wherein at least 50% of the biomolecules in the analysis gel are transferred to the blotting membrane in less than 15 minutes, in less than 10 minutes, or in less than 6 minutes.

10. The method according to claim 1, wherein at least 50% of the biomolecules in the analysis gel are transferred to the blotting membrane in about 5 minutes.

11. The method according to claim 1, wherein substantially all of the biomolecules in the analysis gel are transferred to the blotting membrane in less than about 15 minutes.

12. The method according to claim 1, wherein substantially all of the biomolecules in the analysis gel are transferred to the blotting membrane in less than about 10 minutes.

13. The method according to claim 1, wherein the first electrode comprises a conducting polymer, platinum, stainless steel, carbon, graphite, aluminum, copper, silver, or lead.

14. The method according to claim 1, wherein the second electrode comprises a conducting polymer, platinum, stainless steel, carbon, graphite, aluminum, copper, silver, or lead.

15. The method according to claim 14, wherein the first and the second electrodes comprise copper.

16. The method according to claim 14, wherein the first and the second electrodes comprise carbon.

17. A pre-packaged electroblotting kit comprising a first ion reservoir comprising an ion source sufficient for driving electrophoresis juxtaposed with a blotting membrane, said first ion reservoir being juxtaposable with a first electrode.

18. The pre-packaged electroblotting kit according to claim 17, further comprising a second ion reservoir comprising an ion source sufficient for driving electrophoresis, said second ion being juxtaposable with the analysis gel and with a second electrode.

* * * * *